(12) United States Patent
Palamadai et al.

(10) Patent No.: US 12,300,388 B2
(45) Date of Patent: May 13, 2025

(54) PREDICTING AND MINIMIZING RISKS ASSOCIATED WITH PERFORMANCE OF PHYSICAL TASKS

(71) Applicant: AT&T Intellectual Property I, L.P., Atlanta, GA (US)

(72) Inventors: Rashmi Palamadai, Naperville, IL (US); Nigel Bradley, Canton, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 251 days.

(21) Appl. No.: 17/820,543

(22) Filed: Aug. 17, 2022

(65) Prior Publication Data
US 2024/0062909 A1 Feb. 22, 2024

(51) Int. Cl.
*G16H 50/30* (2018.01)

(52) U.S. Cl.
CPC .................. *G16H 50/30* (2018.01)

(58) Field of Classification Search
CPC ........ G16H 50/30; G16H 20/30; G16H 40/63; G16H 40/67; G16H 50/20; G16H 50/70
See application file for complete search history.

(56) References Cited

U.S. PATENT DOCUMENTS 11,328,796 B1 * 5/2022 Jain ...................... G16H 10/20
2021/0177324 A1 * 6/2021 Levy ..................... A61B 5/162

* cited by examiner

*Primary Examiner* — Chad A Newton
(74) *Attorney, Agent, or Firm* — Guntin & Gust, PLC; Dana B. LeMoine

(57) ABSTRACT

Techniques are described that facilitate dynamically predicting and minimizing risks associated with performance of physical tasks. In one example embodiment, method comprises obtaining, by a system comprising a processor, current health status information regarding a current health status of an entity and task information regarding a task to be performed by the entity. The method further comprises determining, by the system, a personalized assessment of an ability of the entity to perform the task relative to an environment in which the task is to be performed based on the current health status information and the task information, and determining, by the system, risk information regarding a risk associated with performance of the task by the entity within the environment as a function of the personalized assessment.

20 Claims, 10 Drawing Sheets

PREDICTING AND MINIMIZING RISKS ASSOCIATED WITH PERFORMANCE OF PHYSICAL TASKS

TECHNICAL FIELD

This disclosure relates to computer-implemented systems that facilitate predicting and minimizing risks associated with performance of physical tasks.

BACKGROUND

The use of personal biometric monitoring equipment has increased the ability of individuals to more easily and more accurately collect, track and analyze data relating to the body's response to various triggers. For example, wearable sensors can monitor heart rate during an exercise program and collect and record the heart rate data for further analysis. In addition, wearable movement sensors including fine-tuned accelerometers and gyroscopes combined with pattern analysis have enabled the detection and analysis of user motion. The symbiosis of user motion and biometric analysis facilitates an acute understanding of an individual's physiological responses to various types of events and triggers. As a result, various tools can be established that help to control, improve or accommodate an individual's physical and physiological activity.

DETAILED DESCRIPTION

Figure 1:
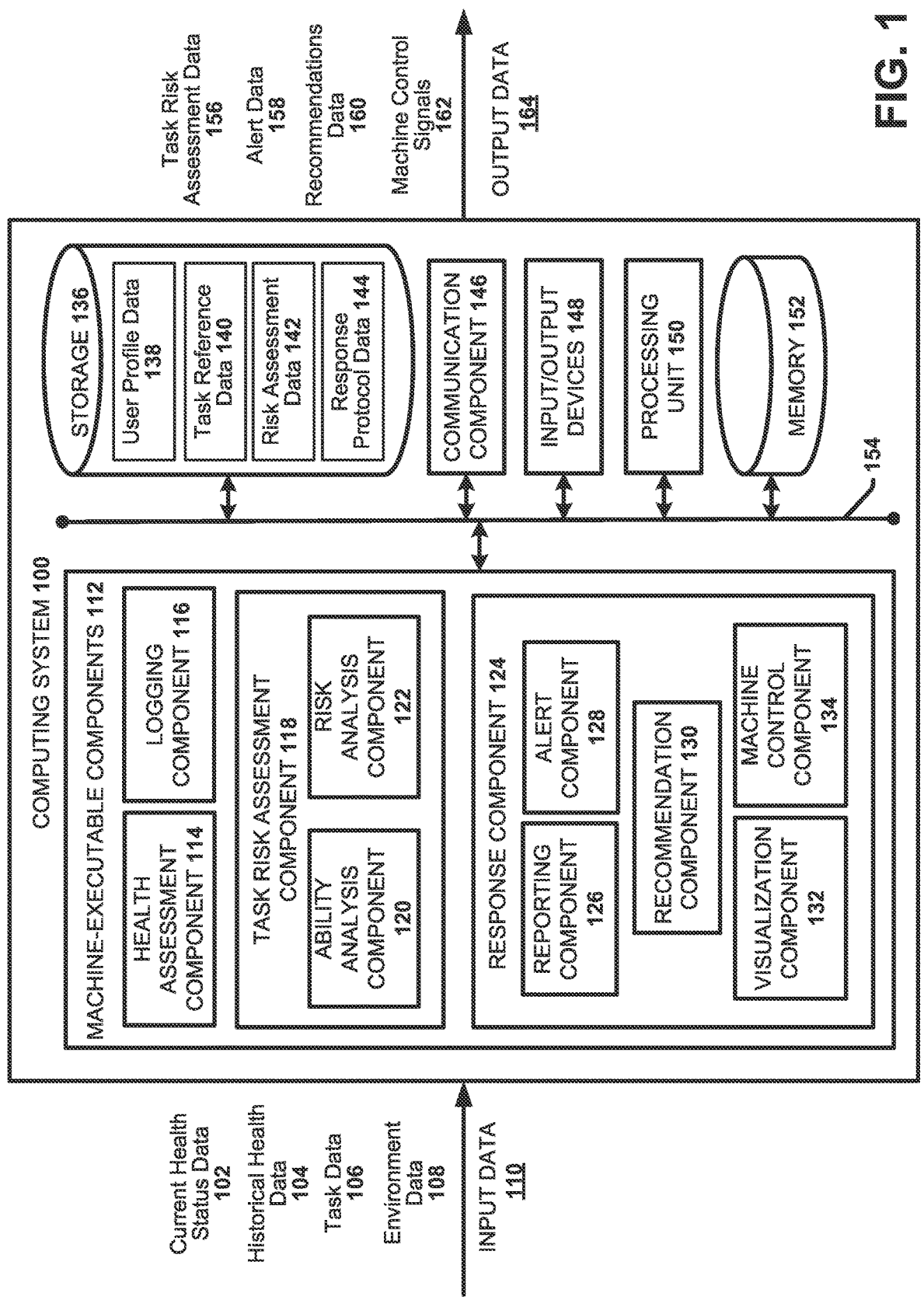
FIG. 1 illustrates an example, non-limiting computing system that facilitates predicting and minimizing risks associated with performance of physical tasks in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, or in this Detailed Description section.

The evolution of wireless communication networks has resulted in an interconnected world of communication devices capable of capturing and communicating a wide range of information about individuals and their environments in real-time as they move about their day. In addition, advancements in machine learning (ML) and artificial intelligence (AI) have facilitated processing such massive amounts of diverse information about individuals to provide a wide range of applications that facilitate daily user activities and decision making in an automated and personalized way. The disclosed subject matter leverages these tools to facilitate predicting and minimizing risks associated with performance of physical tasks by individuals in a variety of different contexts.

To facilitate this end, one or more embodiments of the disclosed subject matter provide a system that obtains and/or determines current health status information regarding a current health status of an entity and task information regarding a task to be performed by the entity. The task can include essentially any task that involves physical performance elements, such as but not limited to, a work-related physical labor task, a daily routine physical task (e.g., daily household chores, errands, personal care tasks, etc.), a fitness or sports related task, and so on. Generally, reference to an "entity" or "user" is used herein to refer to a person/human being. However, the term "entity" as used herein can refer to a person, a group of people (e.g., including two or more), an animal, a machine/device or group of machines/devices. An entity can be represented by a user profile or account that can be associated with one or more systems and/or devices. The current health status information can include information that relates to the physical and mental capabilities of the user to perform the task at hand. In various embodiments, the current health status information can be obtained from medical records for the user, determined from range of motion and other physical performance capabilities tests, determined based on physiological/biofeedback data captured from one or more wearable health monitoring devices, using machine learning, and various other mechanisms. The system can further log and track information regarding the health status of the user over time to facilitate tracking changes in the health status of the entity and predicting future health states of the entity.

The system can further perform a risk assessment regarding risks associated with performing the task, including risks to the physical and/or mental status of the user, risks to other users/entities associated with the environment in which the task is performed, and risks associated equipment and/or machines (e.g., damage or injury thereto) used in the task (e.g., injury to the user of the equipment and/or damage to the equipment), where applicable. Machine learning (ML) and artificial intelligence (AI) can be employed to facilitate various aspects of the risk assessment.

In various embodiments, the risk assessment can involve a personalized assessment of an ability of the user to perform the task relative to an environment in which the task is to be performed based on the current health status information and the task information. The risk assessment can further evaluate and determine risks of potential injuries to the user (e.g., physical and/or mental) that may occur in association with performing the task and the probability of occurrence of the potential injuries based on the current health status of the user and historical health information for the user (e.g., known injuries, known medical conditions, etc.). In this regard, the system can be aware of the physical and mental requirements of the task and the sequence of actions involved in the task (e.g., where applicable) and lines up the user's current health status information against these physical and mental requirements to determine information regarding whether the user is physical and/or mentally capable of performing the task. The system can also be aware of physical performance metric value thresholds that should not be crossed by the user to prevent injury. AI and ML can be applied to understand physical parameters associated with the task, such as body parts involved and physical performance metrics associated with the respective body parts, such as amount of exertion, amount of strength, amount of force, degree of torque, etc. The system can also employ AI and ML to learn body movements/motions used during the task that can cause injury to the user. The system can also employ AI and ML to understand the elative impact of the task on the specific user's body parts and mental status.

This risk assessment can further factor in various contextual factors related to a context of the user in association with performing the task in association with performing the risk assessment. The contextual factors can relate to the environment in which the task is to be performed, such as the location, current weather conditions, time/date, and other people/entities in the environment. The contextual factors can also relate to the type of the environment, such as a work environment, a personal/private environment, a home environment, a place of business, etc. The contextual factors can also relate to any equipment or machines involved in the task.

In some embodiments, based on the risk assessment, the system can generate task risk assessment data regarding the risk assessment and provide the task risk assessment data to the user and/or one or more other entities (e.g., other entities that may be impacted in the environment, a friend/or family member of the user, a caregiver of the user, an employer, an insurance provider, etc.). The task risk assessment data can be used to determine (e.g., by the user, the one or more other entities, and/or the system) whether and how (e.g., potentially with some modification and/or additional safety precautions) the user should proceed with performance of the task. In some embodiments, the system can require the user and/or the one or more other entities to provide acknowledgement feedback indicating that they have received the risk assessment data, reviewed it, and acknowledged/accepted any risks associated with performance of the task by the user. This acknowledgment feedback can be recorded and used to assess liabilities in the event of injuries resulting from performance of the task by the user.

In some implementations, the system can generate an overall risk score based on the risk assessment that accounts for physical and/or mental risks to the user, other entities and/or equipment in the environment, and the probability of occurrence of these risks. The task risk assessment data can further include a more granular break-down of the identified risks. For example, the task risk assessment data can include information regarding all identified risks, magnitude of the respective risks, personalized reasons for which the risks are based (e.g., physical and/or mental health status factors, environmental factors, other contextual factors, etc.), and information indicating the probability of occurrence of each of the identified risks. In some implementations in which the risks include bodily injury to the user, the task risk assessment data can include a visualization of the human body with visual indicators highlighting the specific body part or parts impacted, the manner and degree in which the task impacts each body part in detrimental way to the user, and the probability of injury associated with each body part.

The system can further facilitate minimizing and/or preventing identified risks associated with performing a task by a user. In some embodiments, the system can determine and recommend one or more actions determined to minimize the overall risk score. For example, such actions can relate to becoming more physically and/or mentally prepared to perform the task (e.g., performing stretching, warm-ups, etc.), adjusting one or more physical elements or aspects of the task (e.g., an amount of weight lifted, distance run, movements involved in the task, sequence of the movements, etc.), adding safety precautions (e.g., gear, clothing, equipment/tools, live user monitoring, etc.), changing equipment used in the task, and so on. In some embodiments, the system can provide the user with a recommendation regarding whether the user should proceed with performing the task or not based on the overall risk score. For example, the system can instruct the user not to proceed with the task or to proceed with the task based on the overall risk score falling above or below a threshold risk score. In some implementations, the system can also notify one or more other entities (e.g., a friend/family member, a designated caregiver, emergency services, an employer, other users in the environment that may be impacted by the risky user, etc.) regarding a user associated with a high-risk score (e.g., relative to a defined threshold) relative to performing a particular task so that they may intervene as deemed appropriate. For example, the system can notify one or more friends of family members of that a particular user is about to perform a task determined to be associated with a high risk. In another example, the system can notify other users that there is an individual located in their environment performing or about to perform an activity that may put them at risk. In some implementations, the system can provide notifications to these other entities via one or more social networks (e.g., integrating with the user's designated social network connections to notify them regarding risky activity of user). In some embodiments in which the task involves usage of a machine or electronic equipment, the system can remotely control the machine or equipment to minimize the risk (e.g., preventing a usage of the machine by the user via disabling a functionality of the machine, shutting of the power supply, logging the user out, etc.). In this regard, the system can identify potential issues/risks associated with performing physical tasks by users, communicates the risks to the users and/or the appropriate entities, suggests alternatives to get into the appropriate physical/mental state to perform the task, and/or actively facilitate preventing the user from performing the activity altogether.

The system can further track and monitor user activity and behavior over time, employing a continuous feed-back loop to regularly reassess and evaluate their health status and changes thereto. For example, the system can timestamp, and log all (or portions thereof) received and/or system generated data for a user over time in association with performing task risk assessments with respective user profiles for the users. In some embodiments, the system can further monitor and track (e.g., record) user activity data related to performance (or non-performance) of tasks after providing them with task risk assessment data. The system can also track information regarding physical and/or mental performance measures of the user with respect to performing tasks and impact on the task on the user's physical and/or mental status (e.g., including positive and negative (i.e., injuries) impacts. The system can further regularly process logged/tracked user data using ML and AI to refine and optimize the risk assessment of different tasks relative to specific user profiles. In some embodiments, this can involve the generation of one or more prediction models tailored to perform aspects of the risk assessment based on learned correlations in the tracked user data.

In this regard, the disclosed system provides risk analysis and recommendations to a user who wants to take a more independent evaluation of personal health and lifestyle choices. By understanding the risk of performing an activity or task, a user can receive recommendations on what can be done to remedy the situation or take the recommendation to avoid the task entirely because the risk is too high. At the same time, user can understand their own personal health status and risk of developing progressive diseases due to their lifestyle choices. This can act as a "wake up call" for user to start taking more aggressive steps to improve health.

For example, in a situation where a user wants to understand their risk for doing a specific activity, they can rely on a system to pull from their medical records, their current state of health and the task that is being performed to create a risk profile that the user can then choose to take into consideration. For example, the system and allow a user to understand whether they can or should perform a particular physical task before they attempt it, such as, "can I run 5 miles today?" or "can I lift this 40-pound box from my car to inside my house?" In a situation where the user is susceptible to progressive diseases based on their genetics and lifestyle choice, the system revises the risk assessment based on lifestyle changes. For example, a person's medical history may indicate they are prone to getting diabetes, but due to an active lifestyle change, they are now at a lower risk for getting diabetes by a certain age. In a workplace situation where employees are expected to perform physical labor/tasks, the system can determine the probability that a person would get injured performing a particular task based on their medical history and current physical state. In another example, in a situation where a user's mood is off—which is determined by social media tie in and/or wellness check/system scan—the system can intervene and makes a recommendation to participate in a specific activity or reach out to social network to get back into a good mental well-being state.

The terms "algorithm" and "model" are used herein interchangeably unless context warrants particular distinction amongst the terms. The terms "artificial intelligence (AI) model" and "machine learning (ML) model" are used herein interchangeably unless context warrants particular distinction amongst the terms.

Embodiments of systems and devices described herein can include one or more machine-executable components or instructions embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. These computer/machine executable components or instructions (and other described herein) can be stored in memory associated with the one or more machines. The memory can further be operatively coupled to at least one processor, such that the components can be executed by the at least one processor to perform the operations described. In some embodiments, the memory can include anon-transitory machine-readable medium, comprising the executable components or instructions that, when executed by a processor, facilitate performance of operations described for the respective executable components. Examples of said and memory and processor as well as other suitable computer or computing-based elements, can be found with reference to FIG. 10 (e.g., processing unit 1004 and system memory 1006 respectively), and can be used in connection with implementing one or more of the systems or components shown and described in connection with FIG. 1, or other figures disclosed herein.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting computing system (hereinafter system 100) that facilitates predicting and minimizing risks associated with performance of physical tasks in accordance with one or more embodiments of the disclosed subject matter. System 100 includes machine-executable components 112, storage 136, communication component 146, input/output devices 148, processing unit 150 and memory 152. System 100 further includes a system bus 154 that couples the machine-executable components 112, the storage 136, the communication component 146, the input/output devices 148, the processing unit 150 and the memory 152 to one another. In some embodiments, machine-executable components 112 can be stored in memory 152 and executed by processing 150 to cause the computing system 100 to perform operations described with respect to the corresponding components. In this regard, the computing system 100 can correspond to any suitable computing device or machine (e.g., a communication device, a desktop computer, a personal computer, a smartphone, a server, a virtual computing device, etc.), or interconnected group of computing devices/machine (e.g., interconnected via wired and/or wireless communication technologies).

The storage 136 can store a variety of information that is received by, used by, and/or generated by the computing device 100 in association with predicting and minimizing risks associated with performance of physical tasks. In the embodiment, shown, this information includes (but is not limited to), user profile data 138, task reference data 140, risk assessment data 142 and response protocol data 144. The storage 136 can correspond to any suitable machine-readable media that can be accessed by the computing system 100 and includes both volatile and non-volatile media, removable and non-removable media implemented in any method or technology for storage of information, such as computer-readable instructions, data structures, models, algorithms, program modules, or other data. Computer storage media can include, but is not limited to, random access memory (RAM), read only memory (ROM), erasable programmable read only memory (EPROM), flash memory or other memory technology, digital video disk (DVD) or other optical disk storage, magnetic cassettes, magnetic tape, magnetic disk storage or other magnetic storage devices, or any other medium which can be used to store the desired information and which can be accessed by the computing system 100.

The communication component 146 can correspond to any suitable communication technology hardware and/or software that can perform wired and/or wireless communication of data between the computing system 100 and other systems and devices. In this regard, the communication component 146 can provide for receiving input data 110 from one or more external systems and/or devices and communicating (e.g., sending, transmitting, etc.) output data 164 to one or more external systems and/or devices. Examples of suitable communication technology hardware and/or software employable by the communication component 146 are described infra with reference to FIG. 10. The input/output devices 148 can correspond to any suitable input and/or output device (e.g., a keyboard, a mouse, a touchscreen, a display, etc.) that provides for receiving user input in association with usage of the features and functionalities of the computing system 100 and displaying or rendering information (e.g., in a visual format via a display, as audio, etc.) to users. Examples of some suitable input/output devices 146 are also described with reference to FIG. 10 with respect to input devices 1028 and output device 1036).

The machine-executable components 112 can include health assessment component 114, logging component 116, task risk assessment component 118, ability analysis component 120, risk analysis component 122, response component 124, reporting component 126, alert component 128, recommendation component 130, visualization component 132 and machine control component 134.

The health assessment component 114 can assess the current health status of users. This can involve receiving, aggregating and/or processing any information available for a user that relates to their current health status and generating a current health status profile for the user. Information regarding a user's current health status can be recorded in user profile data 138 for the user (e.g., via logging component 116) and associated with a timestamp that indicates the timing at which the user's health state reflected the current health status information. In this regard, respective users can be associated with distinct user profiles in the user profile data 138 in which any information received and/or generated by system 100 relative to the respective users can be aggregated, logged and stored.

The current health status profile for a user can include information that relates to the current physical and mental health status of the user. The current physical health status information can include information that relates to current the physical abilities of the user to perform essentially any physical task. For example, the current physical health status information can include a wide range of parameters (and their current values) that provide a measure of physical capabilities or functionality of the user, including general physical capabilities to perform daily routing physical tasks (e.g., walking, driving, eating, dressing, sitting, etc.) and physical capabilities to perform more strenuous physical tasks, such as fitness related tasks (e.g., fitness capabilities). In this regard, the physical capability measures can include various measures of physical aptitude, including one or more measures of cardiorespiratory health or (e.g., cardiorespiratory endurance), musculoskeletal fitness (e.g., bone resistance, muscle resistance, muscle strength, stability, agility, balance, reflexes, speed, gait, etc.), and flexibility (e.g., range of motion of respective body parts). The physical capability measures can also include information pertaining to the functional capabilities of the body in totality and the functional capabilities of individual body parts. The current health status information can also include measures of health of different body systems and body organs. The current health status information can also include various physiological parameters (e.g., resting heart rate, blood pressure, pulse, energy level, fatigue level, hormone levels, stress level, blood sugar level, temperature, etc.). The current health profile information can also include current body measurement parameters, including but not limited to, height, weight, body mass index (BMI), muscle mass, muscle density, body fat percentage, and the like. The current health profile information can also include general measures of a user's current activity level (e.g., a measure of degree of how active or sedentary the user's lifestyle), fitness level, strength level, current energy level, current stress level, current fatigue level, hydration level, and so on. The current health profile information can also include one or more measure of the use's sensory system abilities (e.g., strengths and weaknesses with respect to vision, hearing, taste, smell, touch, pain, temperature, proprioception and pressure) and various other current human motor movement measures.

The current health profile information can further include information regarding current (e.g., existing) physical limitations and injuries of the user and current medical conditions of the user. The current health profile information also include current medications taken by the user. The current health profile information can also include various measures of a user's current mental health and state and current mental conditions/diseases of the user. The current health profile information can also include information regarding a user's current mood and/or mood levels, attention level, focus level, and intelligence level.

In the embodiment shown, the computing system 100 can receive current health status data 102 for a user as input data 110. The current health status data 102 can include information that corresponds to a user's current heath profile and/or used to determine one or more measures of a user's current health profile by the health assessment component 114. In this regard, in some embodiments all or portions of a user's current health profile information may be received the computing system 100 (e.g., as current health data 102) from one or more external sources, such as existing medical records (e.g., electronic health records, electronic medical records, etc.). Additionally, or alternatively, all or portions of a user's current health profile information may be provided as user input (e.g., as current health data 102) from the user directly and/or an agent of the user (e.g., friend, family member, designated caregiver, etc.). Additionally, or alternatively, all or portions of the a user's current health profile information can be determined by the health assessment component 114 based on received physical and physiological data for the user captured from one or more health monitoring devices worn by and/or associated with the user, determined based on analysis of information provided in the historical health data 104 for the user (e.g., which may also be received as input 110) using machine learning, determined based on range of motion tests and other physical performance capabilities tests, determined based on medical imaging scan data and various other mechanisms. The historical health data 104 can include historical medical records for a user, such as information regarding past medical conditions/diagnosis, procedures, and past health status information. The logging component 138 can further associate the historical health data 104 for a user with their user profile. The historical health data 104 can be used to extract information regarding comorbidities and persistent injuries, and chronic conditions, and other health status parameters that remain existing factors of the user's current health profile. The historical health data 104 can also be used to evaluate changes in the user's health state over time.

In some embodiments, the health assessment component 114 can assess and determine the current health status profile for a user in association with performing a task risk assessment for a task the user may perform. For example, the health assessment component 114 can assess and update the current health profile information for a user each time the user indicates a task they would like to perform or initiates performing. In other embodiments, the health assessment component 114 can assess and update the current health status of a user on a routine basis (e.g., daily, once a week, once a month, etc.), randomly and/or continuously as new current health status data 102 for the user is received by the system 100. In this regard, it should be appreciated that some measures of a user's current health profile will not vary at or significantly over time (e.g., chronic conditions and persistent injuries) while others may vary throughout the day, week, month, year, etc. The logging component 116 can further log and track changes to a user's current health profile information (e.g., with time/date and context information) as updates are made over time.

The task risk assessment component 118 can perform a risk assessment regarding risks associated with performance of physical tasks by users based on their current health status profile. The risk assessment can evaluate risks to the physical and/or mental status of the user (e.g., injury to the user), risks to other users/entities associated with the environment in which the task is performed, and risks associated equipment and/or machines (e.g., damage or injury thereto) used in the task (e.g., injury to the user of the equipment and/or damage to the equipment), where applicable. The tasks can include essentially any task that involves physical performance elements, such as but not limited to, a work-related physical labor task, a daily routine physical task (e.g., daily household chores, errands, personal care tasks, etc.), a fitness or sports related task, and so on. In various embodiments, the task risk assessment component 118 can perform the risk analysis based on and/or in response to reception of task data 106 that identifies or indicates a particular task to be performed by a user. With these embodiments, the computing system can receive the task data 106 prior to initiation of the task by user. In other embodiments, the computing system 106 can receive the task data 106 in response to initiation of the task and/or during performance of the task.

Still in other embodiments, the task risk assessment component 118 can employ information provided in a user's profile identifying or indicating one or more tasks the user performs or may perform throughout the user's day, week, month, etc. and timing of performance of the tasks. This task information can be provided by the user, determined based on the user's schedule, learned over time using ML based on tracked user activity regarding the task the user regularly performs and/or determined based on information provided by other system or entities regarding the user's potential upcoming tasks and activities (e.g., social media sources, event registration systems (e.g., registering to participate in a fitness event or activity or another type of event involving one or more physical tasks), other friends/family, etc.). With these embodiments, the task risk assessment component 118 can perform risk assessments for the respective tasks at any time before the initiation of the tasks by the user.

In this regard, the manner in which the task data 106 is received by the computing system 100 can vary. For example, in some implementations the system 100 can receive the task data 106 as user input (e.g., provided by the user to perform the task or another entity). For instance, a user may provide input as an inquiry requesting the system to evaluate their ability to perform a task and any associated risks (e.g., "Can I run 5 miles today"). In another example, a first user may provide input as an inquiry requesting the system to evaluate the ability of a second user to perform a task and any associated risks (e.g., "Can my mother run 5 miles with me today?," "Is my employee John Doe fit to work the assembly line today," "Evaluate the risks associated with my handman performing tasks X, Y and Z on my property today." Etc.). In accordance with these examples, authorization can be given by users (e.g., in their profile data or in another manner) that controls what other users can provide such inquires on their behalf, receive task risk assessment data 106 pertaining to themselves, and the contents of the task risk data 106 (e.g., which can vary depending on permissions granted).

Additionally, or alternatively, the task risk assessment component 118 can employ ML and AI to predict or infer a task about to be performed by a user based on a context of the user and tasks performed by the user and/or other users in similar contexts and/or based on monitored user behavior and activity data. The context can relate to an environment of the user (e.g., provided and/or determined based on received environment data 108), a location of the user, a current time/date, a mobility state of the user, a movement pattern of the user, and various other contextual parameters. For example, the task risk assessment component 118 can predict a user is about to perform hot yoga based on being located at a yoga studio at or near the start time of the next class. In another example, the task risk assessment component 118 can predict a user is about to go on a particular amusement park ride based on detection that the user has passed through the ride entry gate.

Still in other embodiments, the task risk assessment component 118 can employ information provided in a user's profile identifying or indicating one or more tasks the user performs or may perform throughout the user's day, week, month, etc. and timing of performance of the tasks. This task information can be provided by the user, determined based on the user's schedule, learned over time using ML based on tracked user activity regarding the task the user regularly performs and/or determined based on information provided by other system or entities regarding the user's potential upcoming tasks and activities (e.g., social media sources, event registration systems (e.g., registering to participate in a fitness event or activity or another type of event involving one or more physical tasks), other friends/family, etc.). With these embodiments, the task risk assessment component 118 can perform risk assessments for the respective tasks at any time before the initiation of the tasks by the user.

In one or more embodiments, the risk assessment performed by the task risk assessment component 118 can involve a personalized assessment (e.g., performed by the ability analysis component 120) of an ability of the user to perform a particular task based on the current health status profile of the user and information defining or indicating health status demands or requirements of the task (e.g., provided in task reference data 140). In some embodiments, the personalized assessment of the ability of the user to perform a particular task can also account for environmental factors, such a weather conditions, and equipment, machines, and/or tools involved in performance of the task (e.g., included in environment data 108). The risk analysis component 122 can further evaluate and determine information regarding any risks associated with performance of the task by the user as a function of the personalized assessment.

In this regard, the task reference data 140 can include information defining a plurality of different tasks and known health status demands and/or requirements of the different tasks. For example, the known health status demands and/or requirements can include information defining or indicating one or more optimal or preferred physical and/or mental ability criterion of the respective tasks (e.g., physical and/or mental capability performance parameters and corresponding parameter values or value ranges). For instance, the physical ability criteria can relate to range of motion measures, strength measures, resistance measures, cardiovascular health measures, balance and stability measures, flexibility measures, height and weight measures, skill level measures, vision capabilities, and various other physical capability performance metrics. In another example, the mental ability criteria can relate to mood measures (e.g., with respect to mood type and/or degree), focus level, mental fatigue level, mental clarity level and various other mental capability performance metrics. In some embodiments, the task reference data 140 can be determined and/or learned for the different task using ML and AI techniques based on analysis of domain knowledge associated with the respective tasks (e.g., medical data, expert options, etc.) describing and/or indicating optimal or preferred physical and/or mental ability criteria of different tasks. Additionally, or alternatively, the task reference data 140 can be determined and/or learned for the different task using ML and AI techniques based on analysis of historical performance data for the respective tasks that provides indications of appropriate and inappropriate physical and/or mental parameters and parameter values for the different tasks. For example, the historical performance data can comprise information regarding the impact of different health status factors (and corresponding capabilities) on the ability of users to perform and/or complete the tasks safely and effectively without mental and/or physical injury and/or undue stress. AI and ML also be applied to understand the relevant physical and/or mental parameters associated with the task, such as body parts involved and physical performance metrics associated with the respective body parts, such as amount of exertion, amount of strength, amount of force, degree of torque, etc. In some embodiments, this historical performance information can include information gathered and generated by the system 100 for a plurality of different users with different health status profiles. Additional details regarding usage of ML and AI by the computing system 100 are described infra with reference to FIGS. 6 and 7.

In this regard, in one or more embodiments, based on information identifying or indicating a particular task to be performed by a user (e.g., the received task data 106 or otherwise determined or predicted by the task risk assessment component 118), the ability analysis component 120 can identify the corresponding health status criteria defined for the task as included in the task referenced data 140. The ability analysis component 120 can further assess whether the user's current health status profile indicates the user is mentally and physical capable of performing the task in line with the health status criteria defined for the task based on comparison of the user's health status profile information with the reference health stats criteria defined for the task. In this regard, the ability analysis component 120 is aware of the physical and mental requirements of the task and the sequence of actions involved in the task (e.g., where applicable) and lines up the user's current health status information against these physical and mental requirements to determine capability information regarding whether the user is physical and/or mentally capable of performing the task. In some embodiments, the capability information can merely indicate whether the user's health status profile satisfies the health capability criteria of the task or not. In other embodiments, the reference health capability criteria can serve as an indication of preferred health capabilities for users performing the task. With these embodiments, the capability information can include a more granular break down of specific criterion where the user is lacking and the degree to the user's health and fitness capabilities differs from one or more of the preferred criteria. For example, the capability analysis component can generate capability information that identifies the relative degree (e.g., a percentage value or another differential metric) to which the user's physical and/or mental capabilities measures matches or satisfies the preferred measures of each criterion of the task (e.g., the user's mental focus level is 10% lower than the preferred level, the user's range of motion is 20% lower than the preferred range, the user's cardiovascular health status satisfies the cardiovascular requirements of the task, etc.).

In some embodiments, based on a determination that one or more of the preferred physical and/or mental health criteria for a task are not met or satisfied by the user's current health status profile as a result of the capability analysis performed by the capability analysis component 120, the task risk assessment component 118 can end the task risk assessment and the response component 124 can perform an appropriate response. For example, the response component 124 can generate and send (e.g., via alert component 128 and communication component 146) an alert (e.g., alert data 158) to the user (e.g., or more specifically, a device associated with the user) informing the user that their current health status is not conducive or appropriate for performing the task and recommending the user not perform the task. Various other responses are envisioned and described in greater detail below with reference to the response component 124.

Additionally, or alternatively, the risk analysis component 122 can continue the task risk assessment and evaluate risks associated with performing the task by the user. The risk evaluation can include determining or inferring one or more risks associated with performing the task by the user. The risks can include (but are not limited to), personal risks to the user performing task, risks to other users or entities associated with the environment in which the task is performed (where applicable), and risks associated equipment and/or machines used in the task, where applicable. The personal risks and the risks to others can include one or more potential physical and/or mental injuries or damage that may occur to the respective users. The risks to other users can also include other negative impacts (e.g., aside from physical and/or mental injury) a user may have on other users in the environment based on as a result of their inability to safely and successfully perform the task (as described in greater detail below). In some embodiments, the risk analysis component 122 can also determine or infer the likelihood or probability of incurring the one or more potential physical and/or mental injuries and/or the equipment/machine damage. The risks associated with the machine or equipment used in the task can include potential damage to the machine or equipment. In some embodiments, the risk analysis can also evaluate costs and losses (e.g., financial costs and other conceivable non-financial costs or losses) associated with the potential injuries (e.g., financial costs of medical treatment and liability reimbursement) risks and/or equipment damage.

In various embodiments, the risk analysis component 122 can evaluate the risks as function of the results of the capabilities analysis. For example, the risk analysis component 122 can determine or infer (e.g., using AI and/or ML techniques) one or more risks associated with performance of the task by the user based on the manner and/or degree to which the user's current health profile deviates from the preferred health status criteria for the task. For example, the risk analysis component 122 can determine or infer one or more potential physical and/or mental injuries the user may incur and the probabilities of incurring the one or more potential injuries in association with performing the task based on the manner and/or degree to which the user's current health profile deviates (or does not deviate) from the preferred health status criteria for the task.

The risk analysis component 122 can also determine or infer the personal injury risks to the user based on the user's current health status profile and/or historical health data 104 for the user (e.g., provided in the user's profile data). For example, the risk analysis component 122 can determine or infer one or more potential physical and/or mental injuries the user may incur based on various other health factors associated with the user that can or may influence incurring an injury, the probability of occurrence of the injury and/or the degree of injury that were not accounted for in the ability analysis. For instance, the various other health factors can include but are not limited to, comorbidities (e.g., existing medical conditions and/or diseases of the user), existing and/or past injuries of the user, and current medications taken by the user. For example, the risk analysis component 122 be aware of physical performance metric value thresholds that should not be crossed by the user to prevent injury or exacerbate an existing injury or medical condition of the user. This information can be provided in respective user profile data for the users and/or defined in the risk assessment data 142. For example, the risk assessment data 142 can include information identifying different medical conditions and existing injuries that users may have (e.g., a described in their medical history data and associated with their profile) and further comprise information defining physical performance metric value thresholds physical performance metric value thresholds that if crossed by the user may result in injury. The risk analysis component 122 can also employ AI and ML to learn body movements/motions used during the task that can cause injury to the user and to understand the elative impact of the task on the specific user's body parts and mental status.

This risk analysis component 122 can further factor in various contextual factors related to a context of the user in association with performing the task in association with performing the risk assessment. Information describing and/or identifying the various other contextual factors associated with the task can be included in environment data 108 received by the system 100 and/or determined by the task risk assessment component 118 based on context data collected from various sources. In this regard, the contextual factors can relate to the environment in which the task is to be performed, such as the location, current weather conditions, supplies and/or equipment available to the user for performing the task (e.g., clothing/apparel, sunscreen, water, gear and various other supplies and equipment relevant to the task), time/date, and other people/entities in the environment. The contextual factors can also relate to the type of the environment, such as a work environment, a personal/private environment, a home environment, a place of business, etc. The contextual factors can also relate to any equipment or machines involved in the task.

For example, the risk analysis component 122 can determine or infer potential physical injuries a user may incur when performing a particular physical task outside in the hot sun as opposed to inside in the air condition. In another example, the risk analysis component 122 can determine or infer that the likelihood of incurring a particular injury is higher based on the location where the task is performed, the time of year, the supplies and/or equipment available to the user, and so. For instance, studies have shown that many otherwise heathy individual capable of shoveling snow suffer from heart attacks and stroke at the beginning of the snow season (e.g., the first snowfall) due to lack of conditioning (e.g., shock to the system). In accordance with this example, the risk analysis component 122 can increase this risk factor for the task of shoveling snow at or near the beginning of the snow season.

In scenarios in which a task to be performed by a user involves one or more other users and/or in which the environment includes other users, the risk analysis component 122 can further determine or infer potential injuries the user may inflict on the other users. This analysis can be based in part on the capability analysis of the user (e.g., whether and to what degree the user is physically and/or mentally capable of performing the task), equipment involved in the task (where applicable) and/or other contextual factors associated with performing the task. In this regard, in various embodiments, the tasks evaluated by system 100 can involve physical tasks performed by a group of users (e.g., a group of two or more users). The group tasks can involve those in which safe (i.e., accident/incident or injury free) and successful performance of the task by at least one or more of the users in the group can be impacted by the physical and/or mental capabilities another user performing the group task. In some of these embodiments, the risk of potential injuries to other users in the group or environment can also include the risk of hindering the safe and successful completion of a group task by other users in the group or environment. For example, consider a whitewater rafting task in which a group of users must work together to navigate a raft safely and successfully through intense white water. If one of the rafters is physically and/or mentally unequipped to perform the task (e.g., as determined based on the capability analysis and/or based on otherwise being determined to be associated with a high risk of injury) the ability of the group to successfully navigate down the river may be substantially hindered and the potential injuries that may be incurred by all rafters can be catastrophic. In another example, consider the scenario involving workers on an assembling line. If one of the workers is unequipped to perform their assembly line task and/or suffers an injury as a result, the tasks of the rest of the workers along the assembling line will be hindered. In accordance with this example, the risk analysis component 122 can assess financial costs associated with the unequipped worker (e.g., costs attributed to assembly line delay and productivity and the like) and incorporate the potential financial costs into the task risk assessment. Thus in various embodiments, the risk analysis component 122 can determine or infer one or more risks (e.g., injuries, inability to safely and successfully perform the group task) a first user may inflict on one or more second users in a group task or environment based on the capability analysis of the first user to perform the group task (e.g., whether and to what degree the user is physically and/or mentally capable of performing the task) and/or the personal risk assessment of the first user (e.g., their personal risks of injury and probability of injury).

The risk analysis component 122 can also assess potential injuries that equipment used to perform a task may inflict on the user performing the task, potential injuries the equipment may inflict on other users in the environment, and potential damage that may occur to the equipment. This analysis can be based in part on the capability analysis of the user (e.g., whether and to what degree the user is physically and/or mentally capable of performing the task), equipment involved in the task and/or other contextual factors associated with performing the task. For example, the risk analysis component 122 can assess potential injuries that equipment used to perform a task may inflict on the user performing the task, potential injuries the equipment may inflict on other users in the environment, and potential damage that may occur to the equipment. This analysis can be a function of the capability analysis of the user performing the task and correlations between deficiencies in one or more physical and/or mental capabilities of the user to perform the task with the corresponding injuries and/or damage. For example, the risk analysis component 122 may determine or infer the risk of one or more injuries to the user and/or other users in the environment attributed to the equipment and/or the risk of damage associated with the equipment is higher based on the user's physical and/or mental deficiencies.

To facilitate the risk analysis aspect of the task risk assessment described above, the risk analysis component 122 can employ risk assessment data 142 and/or machine learning and artificial intelligence. In this regard, in one or more embodiments, the risk assessment data 142 can include information identifying or indicating potential risks associated with performance of the various different tasks the system 100 is adapted to evaluate (e.g., which can include a wide range of different types of physical tasks, from fitness related tasks, daily routine tasks, group tasks, workforce tasks and so on). As noted above, the risks can include personal risks to the user performing the task, risks to others (where applicable), and risks related to damage of equipment used for the task (where applicable). The potential risks associated with each task (or in some implementations one or more) can account for equipment known to be used for the task when applicable and/or scenarios in which other users are involved in or associated with the task. In various embodiments, the potential risks associated with the tasks can be determined and included in the risk assessment data based on analysis of domain knowledge associated with the tasks (e.g., medical data, expert opinions, employer guidelines and protocols, etc.) and/or using ML and AI analysis of historical risk data for the respective tasks. In particular, the historical data can include information that logs actual risks (e.g., injuries, damage, impact on others, etc.) that have occurred in the past based on performance of same or similar tasks by users with different physical and/or mental capabilities measures for the physical and mental capabilities parameters determined relevant for the respective tasks (e.g., as provided in the task reference data 140) in different contexts (e.g., locations, weather conditions, time/date, etc.). The historical data can also log additional medical history factors (e.g., injuries, comorbidities associated with the users when present. In some embodiments, this historical data can be aggregated and generated by the computing system for respective users over time. In this regard, the potential risks can account for essentially all conceivable risks (e.g., injuries, damage, etc.) that have been attributed to the task in all conceivable contexts and for various different health profiles.

The risk assessment data 142 can further include risk probability information that correlates each (or in some embodiments one or more) of the potential risks associated with a task to be performed by a user with their likelihood of occurrence based on different physical and/or mental capabilities measures for the physical and mental capabilities parameters determined relevant for the task (e.g., as provided in the task reference data 140), various additional medical history factors (e.g., injuries, comorbidities, etc.) and/or contextual factors. In this regard, in one or more embodiments, the risk analysis component 122 can employ the risk probability information developed for a task to determine or infer respective probabilities of occurrence of the potential risks associated with the task based on the results of the user's capability analysis, various additional medical history factors (e.g., injuries, comorbidities, etc.) of the user (where applicable) and/or the contextual factors associated with performance of the task by the user. In various embodiments, the manner in which different physical and/or mental capabilities measures for the physical and mental capabilities parameters determined relevant for the task (e.g., as provided in the task reference data 140), various additional medical history factors (e.g., injuries, comorbidities, etc.) and/or contextual factors influence respective probabilities of occurrence of the potential risks associated with a task can be determined using ML and AI analysis of the same historical data described above. In some embodiments, the risk probability information developed for each task can comprise one or more risk models and/or algorithms that account for the learned manner in which different physical and/or mental capabilities measures for the physical and mental capabilities parameters determined relevant for the task (e.g., as provided in the task reference data 140), various additional medical history factors (e.g., injuries, comorbidities, etc.) and/or contextual factors influence respective probabilities of occurrence of the potential risks associated with a task For example, in some embodiments, the risk assessment data 142 can account for the optimal and/or preferred physical and/or mental capability measures determined for a task (e.g., provided in the task reference data 140) such that the optimal and/or preferred physical and/or mental capability measures are selected to minimize the probability of occurrence of each (or in some implementations one or more) of the potential risks associated with the task. For example, the probability associated with each potential risk can be set to an initial baseline probability determined for the optimal physical and/or mental capabilities for the task, wherein the baseline probability for each potential risk represents the average probability of occurrence of the risk at the optimal health profile for the task. The baseline probability associated with each potential risk can (and most likely will) vary. In some implementations, the baseline probability of a potential task risk at the optimal health profile may be zero or another low default probability. Thus, in some implementations, if a user's current health profile indicates they embody the preferred physical and/or mental capability measures for the task, the risk analysis component 122 can determine or infer that the probability of occurrence of each of the potential risks is as low as that observed for such a scenario, which can be set to the corresponding baseline probability for each potential risk.

The risk analysis component 122 can further adjust (e.g., increase or decrease) the probability of occurrence associated with each potential risk based on and/or relative to the degree of deviation between a user's current health profile measures and the optimal or preferred health measures for the task. For example, the risk analysis component 122 can decrease the probability of occurrence of a particular risk even lower than the baseline value based on one or more of the user's physical and/or mental capabilities surpassing (e.g., being even better than) the optimal or preferred criteria. Likewise, the risk analysis component 122 can increase the probability of occurrence of a particular risk even more based on one or more of the user's physical and/or mental capabilities falling below the optimal or preferred criteria. The risk analysis component 122 can further adjust one or more of the respective risk probabilities based on relative impacts attributed to other medical factors not accounted for in the capability analysis (e.g., existing injuries, comorbidities) and contextual factors (e.g., whether, location, time/date, etc.), wherein the manner of adjustment is determined or controlled according to the risk probability information included in the risk assessment data 142.

Thus, in one or more embodiments, the risk analysis component 122 can generate task risk assessment data (e.g., task risk assessment data 156) for a user and a particular task (and context) that identifies respective probabilities of occurrence of one or more potential risks associated with performance of the task. The potential risks can include risks to the user (e.g., one or more physical and/or mental injuries), risks to other users (e.g., where applicable) and risk associated with damage to equipment (e.g., where applicable). In some implementations in which the probability of potential risk is below a threshold value (e.g., 1.0%, 5.0%, 10% or another low-risk probability threshold), the risk analysis component 122 (and/or the reporting component 126) can exclude the potential risk from the task risk assessment data 156.

In some embodiments, the risk analysis component 122 can further determine one or more risk scores for the user and task based on the respective probabilities of occurrence of the one or more potential risks associated with performance of the task. For example, in some implementations, the risk analysis component 122 can generate an overall risk score based on the aggregated probabilities of all the potential risks. Additionally, or alternatively, the risk analysis component can determine overall risk sub-scores for each of the three different risk categories where applicable, that is, a first overall risk for representing risk risks to the user, a second overall risk score representing risks to others, and a third overall risk score representing risk to equipment. The risk analysis component 122 can apply an appropriate weighting scheme for the respective risks in association with generating the risk scores based on their relative severity, importance, cost impact (e.g., financial and/or other costs) and/or various other factors. The weighting scheme can vary for different tasks, different users, and/or different organizations. For example, an employer may use system 100 to monitor and regulate performance of tasks by employees and tailor the weighting scheme that controls the relative impact of different risks on a user's risk score based on the needs and preferences of the employer, defined service level agreements for the employer and so on). In some embodiments, the risk analysis component can generate separate cost information for inclusion in the task risk assessment data that specifically identifies costs (e.g., financial costs) attributed to the potential risks, which can be weighted based on their respective probabilities. In some embodiments, the risk analysis component 122 can generate a more granular break-down of the potential risks including personalized reasons (e.g., primary influential factors) for which one or more of the potential risks are based (e.g., physical and/or mental health status factors, environmental factors, other contextual factors, etc.).

The system 100 can further facilitate minimizing and/or preventing occurrence of potential risks associated with performing a task by a user. In this regard, the response component 124 can provide for performing various responses (i.e., system output data 164) based on the results of the task risk assessment. The responses can be executed based on and/or in response to any of the information determined or inferred in association with performing the capability analysis (e.g., by the capability analysis component 120), and/or the risk analysis (e.g., by the risk analysis component 122). To facilitate this end, the response component 124 can include reporting component 126, alert component 128, recommendation component 130, visualization component 132 and machine control component 134. The responses can include, (but are not limited to): generating a report by the reporting component 126 comprising information describing the results of the task risk assessment (e.g., task risk assessment data 156) and providing the report to the user and/or one or more other appropriate entities; generating and sending an alert (e.g., alert data 158) to the user and/or one or more other entities by the alert component 128 based on and/or in response to the results of the task risk assessment satisfying an alert criterion (e.g., a degree of deviation of the user's current health profile from the preferred health status criteria for the task exceeding a threshold, a task risk score exceeding a threshold, one or more of the risk probabilities exceeding a threshold risk probability, etc.); determining a recommendation (e.g., recommendations data 160) regarding whether and how (e.g., with some modification, with additional safety precautions, etc.) the user should or should not proceed with the task and providing the recommendation to the user (e.g. via recommendation component 130); generating and providing the user with a visualization (e.g., which can be included in/with the task risk assessment data 156) illustrating how the task impacts the user's physical and/or mental health (e.g., via visualization component 132, the); and remotely controlling equipment and/or machines associated with the task based on the results of the task risk assessment (e.g., via the machine control component 134).

The specific responses performed by the response component 124 and the timing of delivery of the respective responses can vary based on the specific results of the task risk assessment, the task evaluated, the user or users involved in the task, user preferences (e.g., provided in the user profile data 138), the task environment, and various other contextual factors. In some embodiments, the response protocol data 144 can provide defined rules and/or protocols that control the responses provided by the response component 124 as a function of various criteria (e.g., the specific results of the task risk assessment, the task, the user or users involved in the task, the environment, user preferences, and various other contextual factors). The response protocol data 144 (and/or user profile data 138) can also include information that identifies and controls who (i.e., what users, entities and/or machines/devices) to send specific responses to (e.g., alert data, task risk assessment data 156 results, recommendation data 160 when (i.e., timing), and the specific information disclosed in the responses.

In this regard, in some embodiments, the recommendation component 130 can be configured to determine and provide the user (and/or one or more other appropriate entities), regarding whether it is recommended the user proceed with performing a task or not based on the results of the task risk analysis. In general, a recommendation that a user should not proceed with can be based on the results of the task risk assessment indicating that performance of the task by the user is attributed to one or more potential risks being too high (e.g., relative to a threshold risk level or risk score), such as the risk of an injury to the user and/or others being too high. It should be appreciated however that a determination of whether or not proceeding with an task is "too risky" can be based on the type of task, the user, the type of risk involved, the severity of the risks, costs associated with the risks, probabilities of the risk occurring, underlying health conditions and/or injuries of the user, a context in which the task is performed, defined acceptable risk levels for the task and entity associated with the task (e.g., employer acceptable risk levels for different tasks performed by employees), and other factors. In various implementations, some or all of these factors can be accounted for in the overall risk score calculation and/or any risk sub-score calculations (e.g., a sub-score representing risk to the user, another representing risks to others, and another representing risks to machines or equipment used in the task). In this regard, in some embodiments, the response protocol data 144 can include information that controls when the recommendation component 130 recommends proceeding with a task or not based on one or more risk scores determined by the risk analysis component as a function of the task risk assessment exceeding a threshold. Likewise, the alert component 128 can be configured to generate and send alerts (e.g., noting "alert, high risks involved, do not proceed with the task,") recommending a user not proceed with performing a task based on the corresponding recommendation determined by the recommendation component and/or a one or more risk scores exceeding a threshold risk score/level considered to render the performance of the task by the user "too risky." However, other basis for recommending proceeding or not proceeding with a task based on the task risk assessment results and/or the user's profile data 138 are envisioned.

For example, in some embodiments, based on a determination that one or more of the preferred physical and/or mental health criteria for a task are not met or satisfied by the user's current health status profile as a result of the capability analysis performed by the capability analysis component 120, the alert component 128 can notify the user and/or one or more other appropriate entities accordingly. For example, the alert component 128 can generate and send an alert (e.g., alert data 158) to the user (e.g., or more specifically, a device associated with the user) informing the user that their current health status is not conducive or appropriate for performing the task and recommending the user not perform the task (e.g., via alert component 128 and communication component 146). In other embodiments, the recommendation component 130 can determine whether the system deems it appropriate or inappropriate for the user to proceed with performing a task based on the some or all of the task risk information determined or inferred by the task risk assessment component 118. For example, the recommendation component 130 can make a recommendation regarding whether the user should proceed with the task or not a function of a combination of the capability analysis results and the risk analysis results. In other embodiments, the recommendation component 130 can be configured to determine whether a user should proceed with a task or not based on one or more of the user's risk scores exceeding a defined risk threshold. In other embodiments, the recommendation can determine and recommend proceeding or forging a task based on specific risk probabilities exceeding a threshold risk probability. In some embodiments, the alert component 128 can be configured to send the user (and/or one or more other entities) an alert informing the user to forgo performing a task based on a determination by the recommendation component 130 that the user should not proceed with the task. In another example, the alert component 128 can be configured to send an alert to one or more other users associated with the task environment that may be impacted by the user performing the task (e.g., "Alert," there is a user performing or about to perform a risky task in your area that may impact you."). In another example, the alert component 130 can be configured to send an alert to a friend or family member regarding a use about to perform or performing a risky task, (e.g., "Alert," your grandmother is about to perform a task deemed high risk.").

In some embodiments, the recommendation component 130 can also determine or infer one more actions for a user to perform that have been determined to minimize the risks and include this information in the recommendations data 160 (e.g., stretching, warming up, using additional safety precautions, etc.). The recommendation component 130 can be configured to determine such injury preventative or risk reduction actions based on one or more risk being too high (e.g., relative to a first threshold) or any level of risk (e.g., recommending actions to lower risks regardless of whether they are high, medium or low). In some embodiments, the recommendation component 130 can be configured to determine one or more actions to minimize one or more risks in association with recommending the user not proceed with the task until the one or more actions are performed. For example, the recommendation component 130 can recommend a user may proceed with a particular task following performance of the one or more risk minimizing actions, such as stretching or warming up (e.g., for fitness related tasks), attaining the proper gear/clothing (e.g., hats, jackets, sunscreen, etc.), and so on. In another example, wherein the current health status information relates to a current mental state or emotional state of the user (e.g., mood, clarity level, energy level, fatigue level, etc.) the one or more risk minimizing actions can comprise one actions predicted to change the current mental state or emotional state of the user (e.g., in a positive way). In some implementations of these embodiments, the system 100 can reassess the user's risk related to performing the task following performance of the recommended risk minimizing actions. For example, the task risk assessment can recalculate the users task risk score and allow (e.g., recommend or otherwise allow via machine control signal activation) the user to proceed with the task based on their recalculated risk score being below an acceptable level and/or their revised tasks risk assessment results satisfying an acceptable criterion.

Information describing particular actions that can be performed to minimize different risks associated with different tasks can be predefined and included in the response protocol data 144, and/or learned (e.g., using ML and AI) based on analysis of historical information identifying different actions taken by users that successfully minimized the corresponding risks. Additionally, or alternatively, these actions can be tailored to specific user profiles (e.g., of similar users with similar demographics, preference, task performance behaviors, etc.) and learned based on similar user profile clustering. Still in other embodiments, these actions can be tailored to individual users and associated with their profile data based on historical data for the user that identifies or indicates past actions performed by the user that facilitated minimizing same or similar risks (e.g., for the same tasks, similar tasks and/or unrelated tasks associated with the same or similar risks) in the past (e.g., as learned and/or determined using ML and AI). For example, as applied to changing a user's current mental or emotional state in a manner that reduces a related risk (e.g., in a positive way conducive to performing the task), the recommendation component 130 can learn past actions performed by the user (e.g., based on tracked data for the user associated with the user's profile) that facilitated the desired change in the user's mental or emotional state in the past.

In some embodiments in which the task involves usage of electronic machines or equipment, the machine control component 134 can remotely control the machine or equipment (e.g., via sending one or more machine control signals 162 to the machine or equipment) in a manner that prevents the user from using the machine or equipment (e.g., deactivating, shutting it down, logging/locking the user out, etc.), or otherwise minimizes a risk associated with usage of the machine or equipment by the user in association with performing the task (e.g., deactivating, changing, or controlling usage of one or more specific functionalities of the machine equipment). In this regard, the manner in which the machine control component 134 controls the equipment can be based on the results of the task risk assessment and be tailored to minimize one or more risks probabilities, and/or determinations regarding whether the user should proceed with the task or forgo proceeding with the task. For example, in some implementations, based on a determination that the user should not perform the task, the machine control component 134 can be configured to deactivate the equipment or otherwise prevent the user from using the equipment to perform the task. In another example, based on a determination that the user may proceed with the task with some modification determined to minimize one or more risks, the machine control component 134 can control a functionality of the machine in a manner effectuates or otherwise results in the modification.

For example, assume the task comprises running on a treadmill, the machine control component 134 can deactivate the treadmill and/or control one or more usage settings of the treadmill, such as a maximum speed, maximum incline and/or duration of usage of the treadmill. The specific manner in which the machine or equipment is controlled and/or adjusted can also be tailored based on the manner and/or degree to which the user's current health profile deviates from the preferred health criteria for the task Continuing with the treadmill example, if the user's cardiovascular health level is 50% lower than the preferred level, the machine control component 134 can control the maximum speed of the treadmill to be a first maximum speed (e.g., 2.0 miles per hour (mph)), whereas if the user's cardiovascular health level is 20% lower than the preferred level, the machine control component 134 can control the maximum speed of the treadmill to be a second maximum speed higher than the first maximum speed (e.g., 4.0 mph).

In some embodiments, the reporting component 126 can also provide information regarding users' task risk assessment results, current health status profile and/or monitored/tracked user task activity (e.g., historically aggregated data for respective users) to one or more authorized third-party entities and/or systems. Information defining and identifying the specific third-party entities to provide this information to and the specific components of the data provided to the third-party entities can be defined in the response protocol data 144 and/or include in respective users' profile data 138 (e.g., in user profile data 138). For example, in some implementations, the reporting component 126 can provide information regarding users' task risk assessment results and/or current health status profile to insurance providers of the respective users. The insurance providers can further employ the information to dynamically determine and adjust insurance policies (e.g., policy type, policy payment premiums and reimbursement information) for the respective users. In association with determining how to adjust and/or set insurance policy information for respective users, the system can aggregate task risk assessment data for the respective users generated over time period and account for patterns and changes in the users' health profile data and/or risk assessment results over time (e.g., lowering premiums for upwards trends of improved health and/or reduced frequency and/or degree of performance of risky tasks, and likewise increasing premiums for downward trends of declined health and/or increased frequency and/or degree of performance of risky tasks). Additionally, or alternatively, the recommendation component 130 can access current insurance policy information for the respective users and determine and recommend appropriated adjustment to insurance policies for the respective users based on their current health status profile and task risk assessment results aggregated over time.

Figure 2:
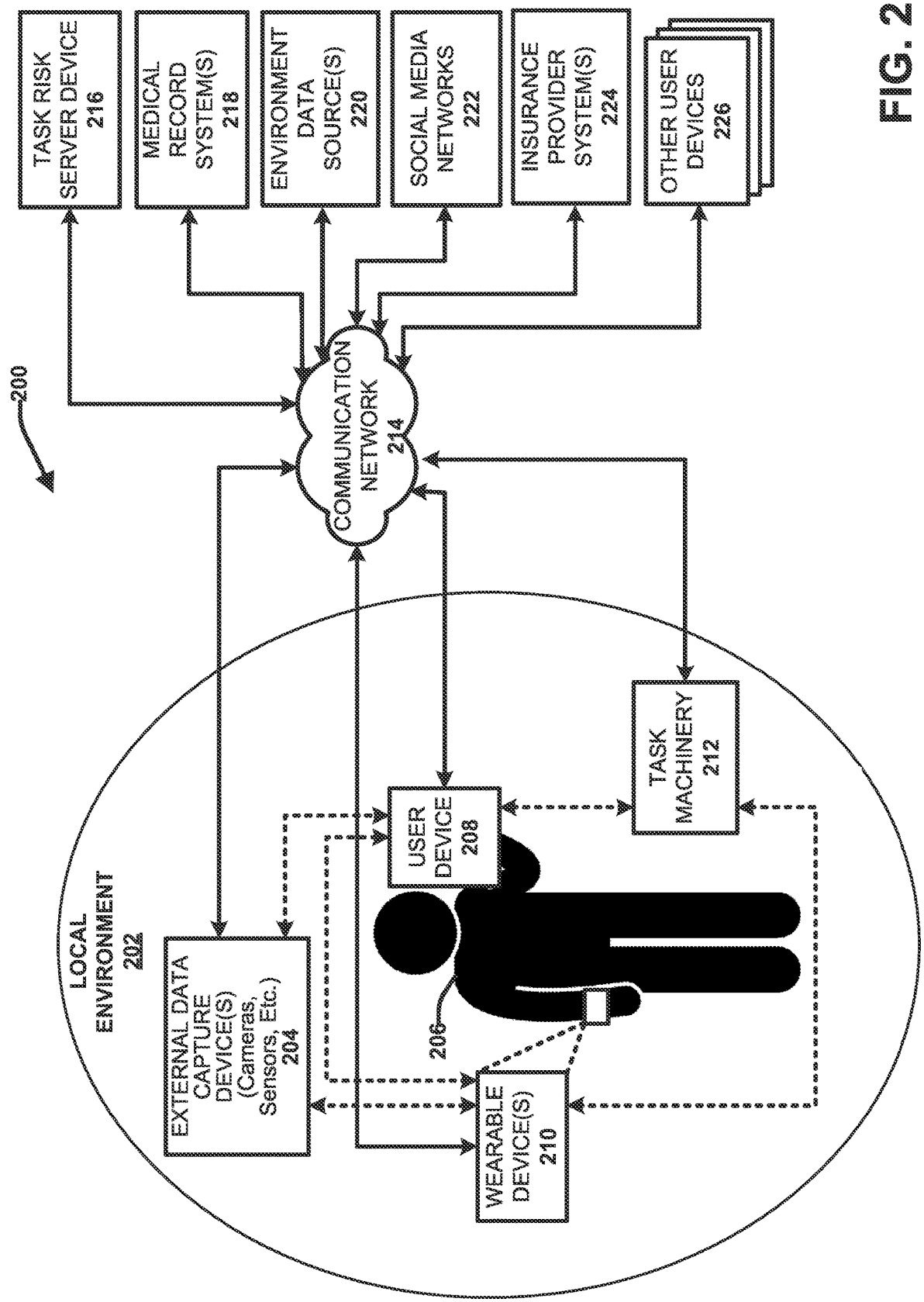
FIG. 2 illustrates an example, non-limiting system that facilitates predicting and minimizing risks associated with performance of physical tasks in accordance with one or more embodiments of the disclosed subject matter.

FIG. 2 illustrates an example architecture diagram of a non-limiting system 200 that facilitates predicting and minimizing risks associated with performance of physical tasks in accordance with one or more embodiments of the disclosed subject matter. With reference to FIG. 2 and FIG. 1, system 200 can include various local devices associated with a user 206 and a local environment 202 in which the user may perform a task that computing system 100 can be employed to evaluate and monitor. The local devices can include a user device 208 associated with the user 206, such as a personal computing device (e.g., a mobile phone, a smartphone, a personal tablet, a laptop computer, etc.), and/or one or more wearable devices 210 associated with the user 210 (e.g., a smartwatch, a health/biometric monitoring device, an augmented reality (AR) eye-ware device (e.g., glasses, goggles, smart lenses, etc.), a virtual reality (VR) eye-ware devices, an extended reality (XR) eye-ware device, one or more other types of wearable sensor devices). The local environment 202 can further include one more external data capture devices 204 (e.g., external to the user 206) that can capture and/or generate information about the user 206 and the local environment 202, such as one or more cameras that can capture image data (e.g., images and/or video) of the local environment 202 and the user 206 and/or one or more other types of data capture devices (e.g., an audio capture devices, chemical sensors, pressure sensors, scanners, analog sensors, digital sensors, infrared sensors, ultrasonic sensors, accelerometers, activity sensors, gaze detection sensors, etc.). The local environment 202 can also include task machinery 212 that can correspond to one or more machines (e.g., devices, equipment, etc.) which may be used in association with performance of a task by the user 206 in some applications and embodiments. Although the local environment 202 depicts a single user 206, it should be appreciated that in many embodiments and implementations the local environment 202 can include one or more other users, including one or more other users that are involved in performance of the task by the user 206 (e.g., a group task) and/or one or more other users that are not involved in the task which may be directly or indirectly impacted by the user's performance (or non-performance) of the task.

One or more of the local devices (e.g., the user device 208, the wearable devices 210, the external data capture devise 204, the task machinery, etc.) may be communicatively coupled to one another via any suitable wired or wireless communication networks and corresponding communication technology (e.g., Wireless Fidelity (Wi-Fi) and BLUETOOTH® wireless technologies, etc.). System 200 further includes various other devices and/or systems external to the local environment 202 that can be communicatively coupled to one another and/or one or more of the local devices via one or more communication networks 214 (e.g., a cellular network, the Internet, etc.). These external systems/devices can include (but are not limited to), task risk server device 216, medical records systems 218, environment data sources 220, social media networks 222, insurance provider systems 224 sand other user devices 226 (e.g., which can correspond to devices of one or more users included in the local environment 202 and/or outside the local environment 202.)

In various embodiments, the computing system 100 and/or one or more elements of the computing system 100 can be deployed and executed by the task risk server device 216. With these embodiments, the task risk server device 216 can collect and/or otherwise receive some or all of the input data 110 from one or more of the local devices (e.g., the user device 208, the one or more wearable devices 210, the one or more external data capture devices 204) and/or the medical records systems 218, the environment data sources 220, the social media networks 222 and/or the other user devices 226 via the communication network 214. The task risk server device 216 can further communicate (e.g., via communication component 146 and response component 124 and the communication network 214) relevant portions of the output data 118 to the user device 208, the other user devices 226, one or more social media networks 222, insurance provider systems 224, etc. (e.g., the task risk assessment data 156, the alert data 158, the recommendation data 160), and/or the task machinery (e.g., the machine control signals 162) in accordance with the response protocol data 144 and/or response rules defined for respective users in their user profile data. For example, the task risk server device 216 can communicate task risk assessment data 156, alert data 158, recommendations data 160, and other information about users' current health status to defined users at their respective social media accounts at one ore more social networks 122, insurance provider system(s) 224, other user devices 226 and/or various other relevant third-party systems. However various other system architectures are envisioned (e.g., local user device deployment architecture, a cloud-deployment architecture and so on).

For example, the task risk server device 216 can interface with one more medical record systems 218 to access and retrieve current health status data 102 and/or historical health status data 104 for users. In some embodiments, the task risk server device 216 can also receive, identify and/or determine information regarding the current health status of a user from one or more social media networks and/or other users (e.g., via other user devices 226). For example, the task risk server device 216 can access and evaluate social media posts, pictures, video and other content to determine or infer information about the user's mental state, mood, context and the like.

Additionally, or alternatively, information regarding the current health status of users (e.g., user 206 and the like) can be received from the user device 208, the one or more wearable devices 210 and/or one or more external data capture devices 204. For example, in various implementations, the user device 208 can be employed by the user 206 to interface with the computing system 100 as deployed at the task risk server device 216 to access and employ the features and functionalities thereof using suitable network-based platform (e.g., a web application, a client application, a mobile application or the like). In some implementations of these embodiments, the user 206 can provide some or portions of the input data 110 as user input via user device 208. For example, the user 208 can provide input identifying or indicating a task they would like to perform (e.g., task data 106), identifying or indicating their current health status (e.g., current health status data 102), identifying or indicating their historical health status data 104, and/or identifying or indicating information about their current environment context (e.g., environment data 108). In some implementations of these embodiments, the task risk server device can perform a task risk assessment for the user and a particular task in response to an explicit inquiry provided by the user identifying or indicating the task (e.g., "Can I run five miles today?", "Can I go whitewater rafting next week?" etc.).

Additionally, or alternatively, the task risk server device 216 can collect and/or receive information regarding the current health status of the user 206 from one or more wearable devices 210 worn by the user. For example, the one or more wearable devices 210 can comprise a health monitoring device worn or otherwise attached to the user 206 that can capture and/or generate physiological data about the user 206 which can indicate or be used to determine one or more current physical and/or mental health status measure of the user 206. The wearable devices 210 can capture and report the physiological data for the user to task risk server device 216 either directly and/or via the user device 208 in real-time or substantially real-time in association with performing various physical tasks. For example, the one or one or more wearable devices can include biometric sensors configured to detect information regarding at least one of: heart rate (e.g., via a heart monitor device), body temperature (e.g., via a thermometer), respiration, perspiration, blood pressure, electrical activity of the heart or brain, mood, energy level, mental state and so one. In another example, the one or more wearable devices 210 can include biosensors configured to detect information regarding at least one of: glucose level, cortisol level, blood oxygen level, blood alcohol level, inflammation, nitric oxide level, drug levels/residues present in the body, pathogens present in the body, or bacteria present in the body. In an aspect, the one or more wearable devices 210 can include implanted medical devices/sensor configured to detect and wirelessly communicate a wide array of biometric information about the user 206 to the user device 208 and/or the task risk server device 216.

In addition to physiological/biometric data, the one or more wearable devices 210 can facilitate capturing and reporting of user movement or motion corresponding to speed, direction, and orientation of the user a whole and/or individual body parts of the user. For example, the one or more wearable devices 210 can include motion sensors such as an accelerometer, a gyroscope or an inertial measurement unit (IMU) configured to capture motion data regarding acceleration, rotation/orientation, and/or velocity of the user and/or respective body parts to which the motion sensors attached. This information can be processed to generate various physical capability performance measure for the user. Additionally, or alternatively, information regarding the current health status of the user can be determined via processing of image data captured of the user 206 (e.g., via one or more external capture devices, and/or one or more cameras associated with the user device 208). For example, image data of the user 206 can be analyzed using two-dimensional and/or three-dimensional image analysis to determine physical measurements metrics for the users, such as height, weight, body fat, dimension of the user's waist, hips, shoulders, biceps, etc. Image data of a user performing various motions and/or physical exercises and task can also be processed to automatically determine physical health performance capabilities and corresponding metric values for the user. Image data captured of the user 206 can also be processed and analyzed to determine information regarding user mood and mental state.

Information regarding the environment of the user (e.g., environment data 108) can also be determined and/or provided by one or more external capture devices 204 and/or the user device 208. For example, image data of the environment captured via one or more cameras associated with either of these devices can be processed using object recognition and/or facial recognition to determine information regarding objects and/or other people in the environment. Additional information about the user's environment can further be determined based in part on the user's current location (e.g., reported by the user device 208 and/or determined using any suitable device location detection mechanisms) and information associated with the user's current location provide in one or more environment data sources 220 (e.g., type of location, tasks performed at the location, places of business at the location, events at the location, current weather, etc.).

In some embodiments, information regarding a task to be performed by the user (e.g., task data 106) can be determined or inferred (e.g., using ML and/or AI) based on any or all of the data captured, provided and/or determined by the local devices associated with the local environment 202 and/or gathered from various external sources (e.g., environment data sources 220, social media networks 222, etc.). For example, the tasks risk assessment component 118 can infer a task about to be performed or being performed by the user 206 based on their current context (e.g., location, time/day, schedule, job/role, movement pattern and activity, etc.) and behavior. For instance, the task risk assessment component 118 can infer a task about to be performed or being performed by the user 206 based on the user's location and historical task activity of the user at the location and/or other users at the location and other information known about the location (e.g., location type (e.g. work vs. home), image data captured of the environment and the user 206, movement/motion data captured of the user, information identifying or indicating other entities and objects in the environment, and various other contextual factors. With these embodiments, the task risk assessment component 118 can monitor the user 206 in real-time as the user moves about their day within the same local environment and/or from place to determine or infer various tasks the user is performing or may perform. The task risk assessment component 118 can further initialize the task risk assessment for the user and a task based on determining or inferring the user is performing the task or about to perform the task. In some embodiments, the task risk assessment can be performed autonomously without notification to the user. For example, the task risk assessment component 118 can regularly and/or continuously assess the user's capability to perform various tasks and associated risks throughout the user's day (or another time period) as new tasks which may be performed by the user are forecasted. In some implementations of these embodiments, the response component 124 can be configured to only notify the user regarding the results of task risk assessment if one or more alert criteria are satisfied, such as the user's capability analysis indicating the user is not capable of performing the task safely and/or successfully, and/or the user's risk analysis indicating one or more risk probabilities and/or risk scores exceeding a threshold. In this regard, as a user goes about their day, system 100 and/or system 200 can be applied to monitor the user and notify and warn the user regarding certain tasks the system deems risky for the user to perform and why, thereby providing a safety guidance tool for the user.

Figure 3:
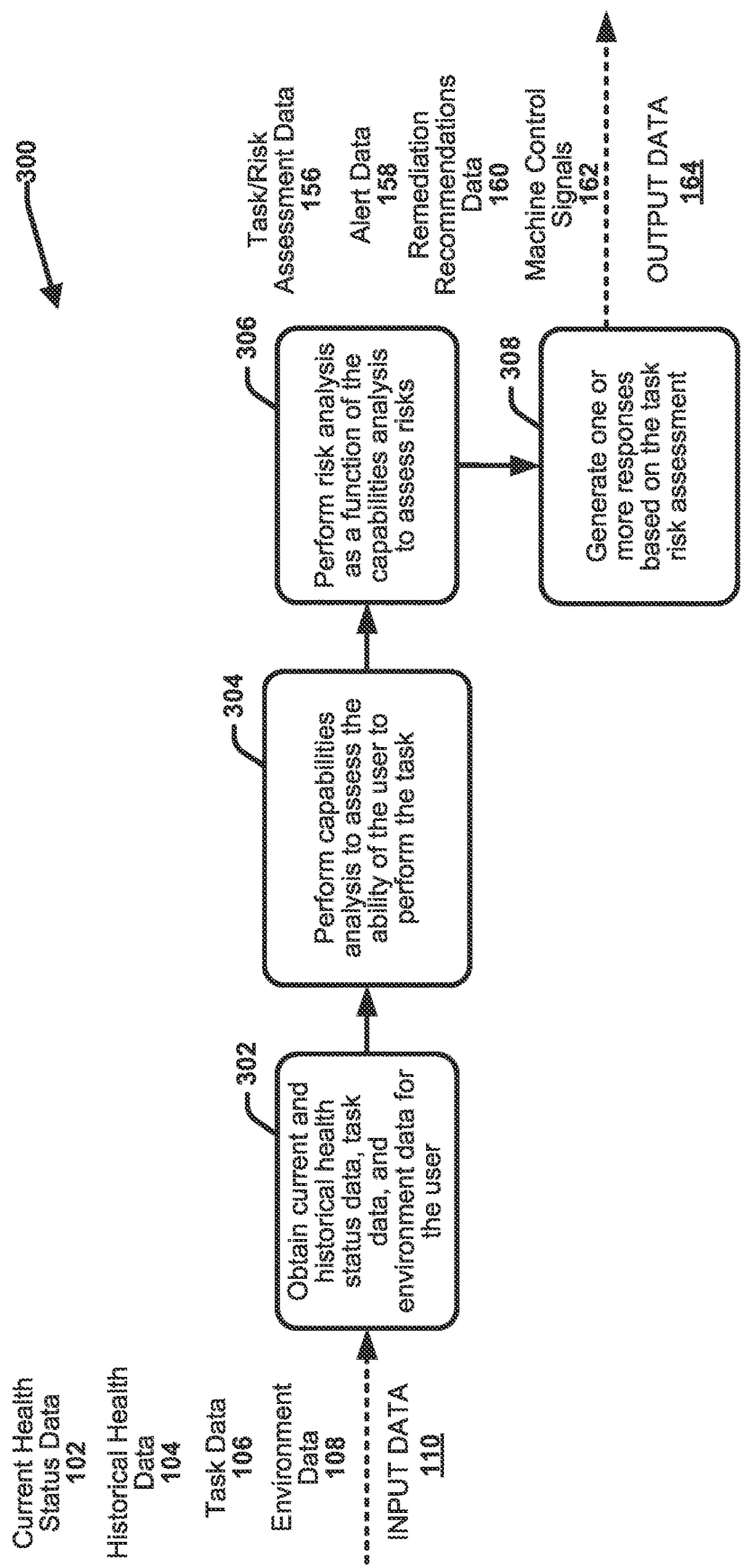
FIG. 3 presents a high-level flow diagram of an example process that facilitates predicting and minimizing risks associated with performance of physical tasks in accordance with one or more embodiments of the disclosed subject matter.

FIG. 3 presents a high-level flow diagram of an example process 300 that facilitates predicting and minimizing risks associated with performance of physical tasks in accordance with one or more embodiments of the disclosed subject matter. In various embodiments, process 300 corresponds an example process that can be performed by computing system 100 and/or system 200. Repetitive description of like elements employed in respective embodiments is omitted for sake of brevity.

In accordance with method 300, at 302, current health status data 102, historical health status data 104, task data 106 and environment data 108 (i.e., input data 110) can be obtained for a user (e.g., by computing system 100 via communication component 146 and/or health assessment component 114). In various embodiments, the logging component 116 can further log all (or some) of the input data 110 received for a user with profile data for the user (e.g., in user profile data 138). In some implementations, some or portions of the input data 110 can be obtained about the user as already associated with the user profile data (i.e., in user profile data 138). At 304, the capabilities analysis can be performed by the ability analysis component 120 to assess the ability (i.e., physical and/or mental) ability of the user to perform the task represented in the task data 106. At 306, the risk analysis component 122 can perform the risk analysis as a function of the capabilities analysis to assess the risks associated with performance of the task by the user. At 308, the response component 124 can generate one or more responses based on the task risk assessment. These responses can include any of the response represented in output data 164.

Figure 4:
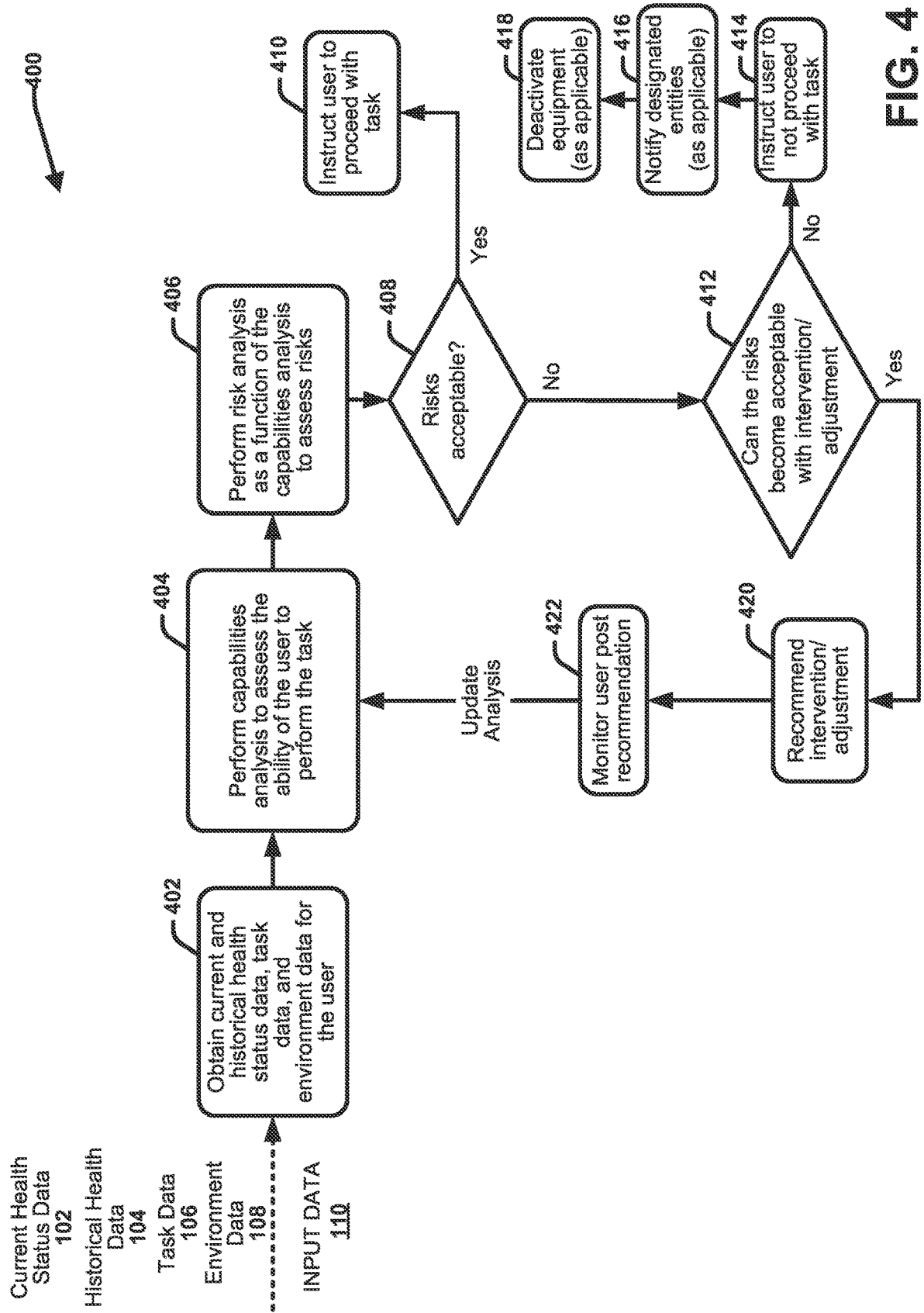
FIG. 4 presents a high-level flow diagram of another example process that facilitates predicting and minimizing risks associated with performance of physical tasks in accordance with one or more embodiments of the disclosed subject matter.

FIG. 4 presents a high-level flow diagram of another example process 400 that facilitates predicting and minimizing risks associated with performance of physical tasks in accordance with one or more embodiments of the disclosed subject matter. In various embodiments, process 400 corresponds an example process that can be performed by computing system 100 and/or system 200. Repetitive description of like elements employed in respective embodiments is omitted for sake of brevity.

In accordance with method 400, at 402, current health status data 102, historical health status data 104, task data 106 and environment data 108 (i.e., input data 110) can be obtained for a user (e.g., by computing system 100 via communication component 146 and/or health assessment component 114). In various embodiments, the logging component 116 can further log all (or some) of the input data 110 received for a user with profile data for the user (e.g., in user profile data 138). In some implementations, some or portions of the input data 110 can be obtained about the user as already associated with the user profile data (i.e., in user profile data 138). At 404, the capabilities analysis can be performed by the ability analysis component 120 to assess the ability (i.e., physical and/or mental) ability of the user to perform the task represented in the task data 106. At 406, the risk analysis component 122 can perform the risk analysis as a function of the capabilities analysis to assess the risks associated with performance of the task by the user.

At 408, the recommendation component 130 can determine whether the risks associated with performance of the task by the are acceptable. For example, the recommendation component 130 can evaluate criteria for the task (e.g., included in response protocol data 144) regarding acceptable risk assessment results warranting performance of the task by the user, such as one or more acceptable risk probabilities and/or one or more acceptable risk score values. If at 408 the recommendation component determines the risks are acceptable, at 410, the recommendation component 130 can instruct the user to proceed with the task. If, however at 408 the recommendation determines the risks are not acceptable, at 412, the recommendation component can determine whether the risks can become acceptable (e.g., meaning that the probabilities of one or more of the potential risks can be minimized to an acceptable degree) with some recommending intervention actions and/or adjustment to the task. If at 412, the recommendation component 130 determines that the risks cannot be minimized sufficiently with intervention (e.g., stretching, warming up, using added safety measures, etc.) and/or adjustment to the task, then at 414, the recommendation component 130 can instruct the user (e.g., via a recommendation notification sent to the user device 208) to not proceed with the task. The alert component 128 can also notify one or more designated entities regarding the recommendation (as applicable), such as friends, families, co-workers, the user's employer, the user's insurance provider, other users potentially impacted, and so on. In some implementations in which the task involves usage of a machine or equipment (e.g., task machinery 212), at 418 the machine control component 134 can also deactivate the equipment.

Alternatively, if at 412 the recommendation component 130 determines that the risks can be minimized sufficiently with intervention (e.g., stretching, warming up, using added safety measures, etc.) and/or adjustment to the task, then at 420, the recommendation component 130 can instruct the user (e.g., via a recommendation notification sent to the user device 208) to perform the recommended intervention and/or adjustment. At 422, the system can monitor the user following the recommendation at 420 to determine whether the user has implemented the recommended intervention and/or adjustment and/or otherwise performed the recommended actions determined to minimize the risks. The system can further update the task risk assessment thereafter to re-assess the risks.

Figure 5:
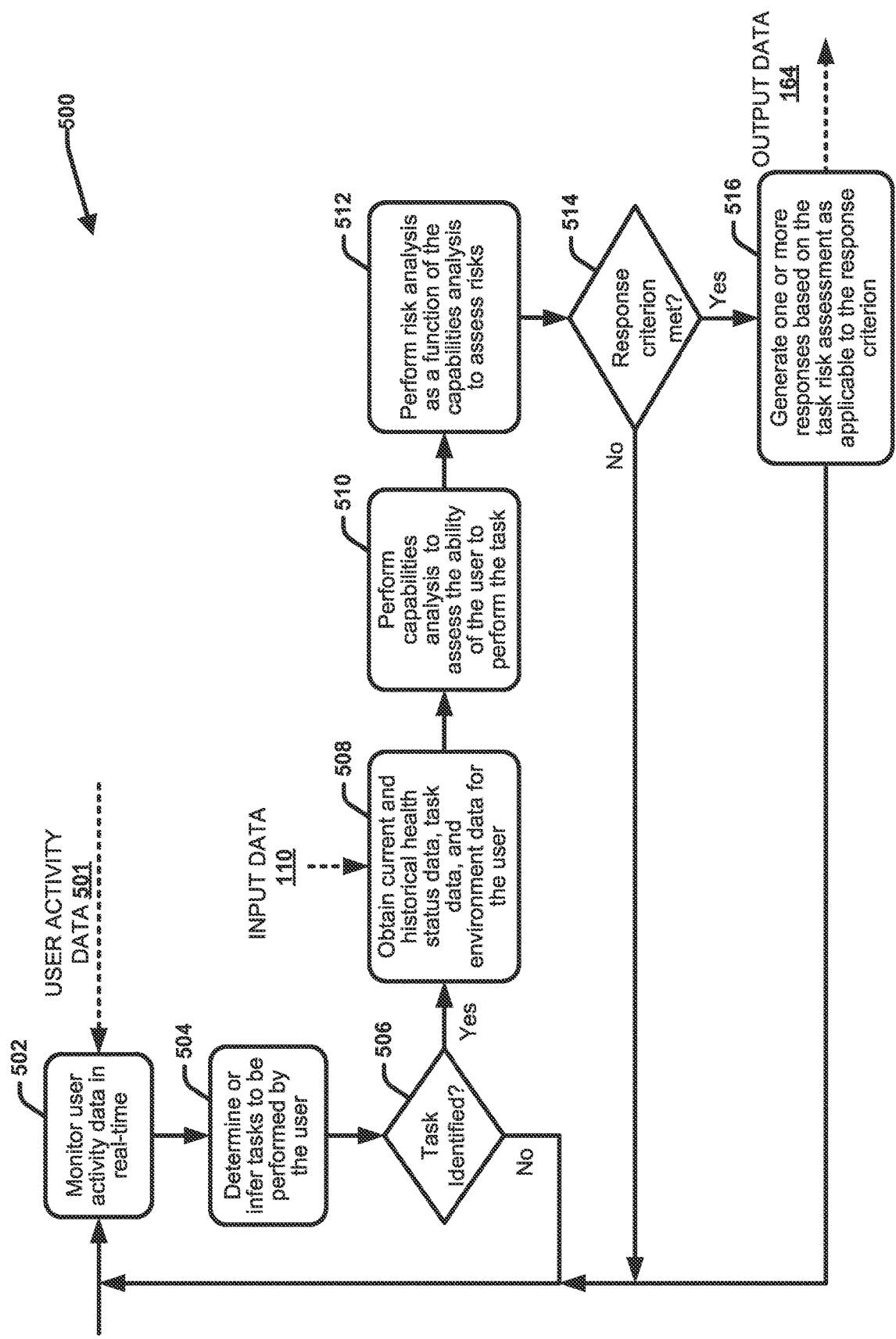
FIG. 5 presents a high-level flow diagram of another example process that facilitates predicting and minimizing risks associated with performance of physical tasks in accordance with one or more embodiments of the disclosed subject matter.

FIG. 5 presents a high-level flow diagram of another example process 500 that facilitates predicting and minimizing risks associated with performance of physical tasks in accordance with one or more embodiments of the disclosed subject matter. In various embodiments, process 500 corresponds an example process that can be performed by computing system 100 and/or system 200. Repetitive description of like elements employed in respective embodiments is omitted for sake of brevity.

In accordance with method 500, at 502, the computing system 100 can monitor user activity data 501 in real time (or substantially real time). The user activity data 501 can correspond to any information related to the real-time activity, state and context of the user that may be used to infer tasks the user may perform throughout their day. Such user activity information can include any information captured and/or determined about the user via one or more devices associated with the user and the local environment (e.g., user device 208, one or more wearable device 210, one or more external capture devices 204, task machinery 212, environment data sources, social media networks 222, and/or other user devices 226. At 504 the system 100 can determine or infer tasks to be performed by the user based on the monitored user activity data 502. For example, the task assessment component 118 can predict upcoming tasks the user may perform in the near future (e.g., within a defined upcoming timeframe) based on the monitored user activity data 501 and learned correlations between various information included in the user activity data 501, such as the user's, location, time of day, behavior, movement pattern, schedule, context, and so on.

In various embodiments, the analysis at 506 can be regularly and/or continuously performed by the task risk assessment component 118 as based on the monitored user activity data 501. In this regard, if at 506 no upcoming tasks are identified, then process 500 can continue with the cycle of monitoring user activity data at 502 and processing the user activity data at 504 to identify upcoming tasks.

However, if a task is identified at 506, that process 500 can proceed in accordance with process 300. In some implementations, prior to 508 the system can provide the user with a prompt asking the user to provide feedback whether they are about to perform the forecasted task (e.g., "Hi John. Are you about to mow the lawn?"). In this regard, at 508 current health status data 102, historical health status data 104, task data 106 and environment data 108 (i.e., input data 110) can be obtained for the user (e.g., by computing system 100 via communication component 146 and/or health assessment component 114). In some implementations, some or portions of the input data 110 can be obtained about the user as already associated with the user profile data (i.e., in user profile data 138). At 510, the capabilities analysis can be performed by the ability analysis component 120 to assess the ability (i.e., physical and/or mental) ability of the user to perform the task identified at 506. At 512, the risk analysis component 122 can perform the risk analysis as a function of the capabilities analysis to assess the risks associated with performance of the task by the user.

At 514, the response component 124 can determine whether any response criterion have been met that indicate a response is warranted based on the results of the task risk assessment. For example, in some embodiments, the response criterion can be based on the one or more potential risks probabilities being too high (e.g., relative to defined thresholds) and/or one or more risk scores being too high (e.g., relative to defined thresholds), such that providing the user with some form of alert or warning regarding the task risk assessment results is warranted. However, the response criterion can vary. If at 514 the response component 124 determines a response criterion is met, then at 516, the response component can generate one or more responses based on the task risk assessment as applicable to the response criterion. These responses can include any of the response represented in output data 164. If, however at 514 the response component determines a response is not needed (e.g., the risk assessment result indicate that no or low risks are present), than process 500 can continue with the monitoring cycle at 502.

Figure 6:
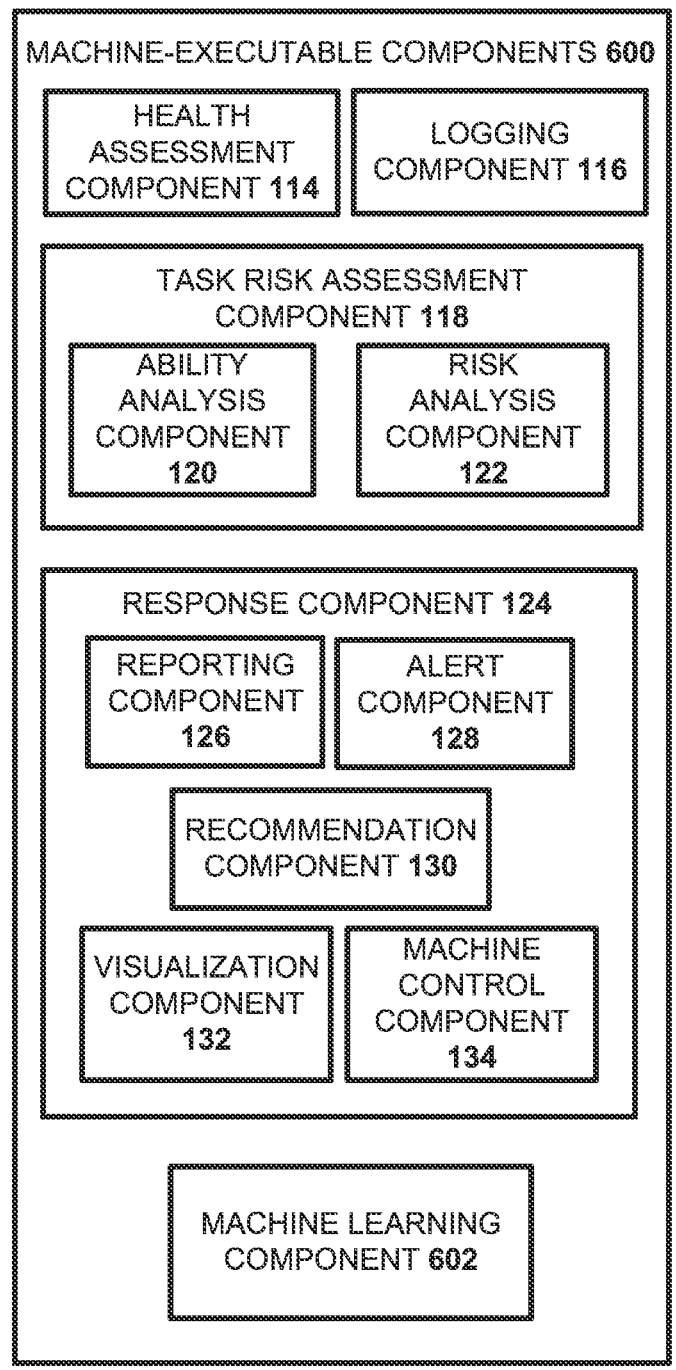
FIG. 6 illustrates example computer-executable components that can facilitate predicting and minimizing risks associated with performance of physical tasks in accordance with one or more embodiments of the disclosed subject matter.

FIG. 6 illustrates example machine-executable components 600 that can facilitate predicting and minimizing risks associated with performance of physical tasks in accordance with one or more embodiments of the disclosed subject matter. Machine-executable components 600 are similar to computer-executable components 112 with the addition of machine learning component 602. In various embodiments, machine-executable components 600 can replace machine-executable components 112 in computing system 100 and/or be executed by the task risk server device 216 of system 200. Repetitive description of like elements employed in respective embodiments is omitted for sake of brevity.

Various aspects of the disclosed subject matter can employ machine learning and artificial intelligence to automatically generate inferences and predictions regarding the task risk assessment processes described herein. To facilitate this end, the machine-executable components 600 can include machine learning component 602.

In some embodiments, the machine learning component 602 can employ ML to facilitate the health assessment performed by the health assessment component 114. As described above, the health assessment component 114 can evaluate current health status data 102 for a user as well as historical health data 104 for the user to generate a current health profile information for the user that describes the user's current physical and mental health status. The current health profile information can comprise various health metrics that measure the physical and/or mental performance capabilities of the user. In this regard, the machine learning component 602 can employ various ML techniques to learn correlations between different physiological parameters, physical parameters, injuries, body measurements (e.g., height, weight, BMI, etc.), and mood and mental state parameters with relevant health metrics that measure the physical and/or mental performance capabilities of the user.

The machine learning component 602 can employ ML to facilitate various aspects of the task risk assessment performed by the task risk assessment component 118. In some embodiments, the machine learning component 602 can employ ML to predict upcoming tasks a user may initiate performing (e.g., within a defined timeframe, such as the next five minutes, the next ten minutes, the next hour, the next 24 hours, etc.). For example, the machine learning component 602 can employ ML to learn correlations between user contexts (e.g., location, time of day, role, weather, environment, other users in the environment, objects in the environment, etc.), and user activity and behaviors (e.g., movement patterns, gestures, motions, interaction with the environment, etc.), user profiles, and tasks performed. The learning can be generalized to all tasks and all users as well as tailored to specific user profiles (e.g., users with same or similar demographics, jobs, schedules, preferences, activities and behaviors, habits, etc.) and/or specific users (e.g., learning correlations between a specific user's context, schedule, and activity with tasks the users perform).

The machine learning component 602 can employ ML to facilitate the capabilities analysis performed by the ability analysis component 120. For example, the machine learning component 602 can employ ML to learn correlations, patterns and/or rules for different tasks regarding physical and/or mental health parameters and associated parameter values preferred for different tasks. For example, the machine learning component 602 can learn the impact of different physical tasks and the sequence of actions associated on the human body. The machine learning component 602 can further learn and define the body parts involved in a task and respective physical performance demands of the task on the anatomy and physiology of the body (e.g., exertion, amount of force, torque, etc.) required to perform the tasks. The machine learning component 602 can also employ ML to facilitate the risk analysis performed by the risk analysis component 122. For example, the machine learning component 602 can employ ML to learn risks associated with different tasks and correlations, rules and/or patterns regarding how different physical and/or mental health parameters and associated parameter values and different contextual factors impact the probabilities of the risks. The machine learning component 602 can further learn how known injuries and/or mental and/or physical limitations can influence these risks. For example, the machine learning component 602 can learn body movements associated with different task that can cause further injury or exacerbate an existing injury (e.g., lifting, twisting, falling, etc.).

The machine learning component 602 can also employ ML to learn and define acceptable risk probabilities and acceptable risk scores. The machine learning component 602 can also employ ML to learn and define correlations between different risks and associated costs on risk score valuations. The machine learning component 602 can also employ ML to learn and define various actions that can be performed to minimize different risks in different contexts.

To facilitate this end, the machine learning component 602 can perform learning with respect to any and all of the data received by the computing system 100 (e.g., input data 110, user activity data 501), stored by the computing system 100 (e.g., user profile data 138, task reference data 140, risk assessment data 142, response protocol data 144) and generated by the computing system (e.g., output data 164). The machine learning component 602 can also evaluate relevant domain knowledge and other relevant information provided by external systems (e.g., medical records systems 218, environment data sources 220, social media networks 222, and so on). Hereinafter, any information received by the computing system 100, generated by the computing system 100 and/or accessible to the computing system 100 is collectively referred to as "collective machine learning data" for the machine learning component 602.

It should be appreciated that machine learning component 602 can perform learning associated with the collective machine learning data explicitly or implicitly. Learning and/or determining inferences by the machine learning component 602 can facilitate identification and/or classification of different patterns associated with the collective machine learning data, determining one or more rules associated with collective machine learning data, and/or determining one or more relationships associated with the collective machine learning data that influence determinations and inferences by the health assessment component 114, the task risk assessment component 118 and the response component 124. The machine learning component 602 can also employ an automatic classification system and/or an automatic classification process to facilitate identification and/or classification of different patterns associated with the collective machine learning data, determining one or more rules associated with collective machine learning data, and/or determining one or more relationships associated with the collective machine learning data that influence determinations and inferences by the health assessment component 114, the task risk assessment component 118 and the response component 124. For example, the machine learning component 602 can employ a probabilistic and/or statistical-based analysis (e.g., factoring into the analysis utilities and costs) to learn one or more patterns associated with the collective machine learning data, determining one or more rules associated with collective machine learning data, and/or determining one or more relationships associated with the collective machine learning data that influence determinations and inferences by the health assessment component 114, the task risk assessment component 118 and the response component 124. The machine learning component 602 can employ, for example, a support vector machine (SVM) classifier to facilitate learning patterns associated with the collective machine learning data, determining one or more rules associated with collective machine learning data, and/or determining one or more relationships associated with the collective machine learning data that influence determinations and inferences by the health assessment component 114, the task risk assessment component 118 and the response component 124. Additionally, or alternatively, the machine learning component 602 an employ other classification techniques associated with Bayesian networks, decision trees and/or probabilistic classification models. Classifiers employed by the machine learning component 602 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, x=(x1, x2, x3, x4, xn), to a confidence that the input belongs to a class—that is, f(x)=confidence(class).

In an aspect, the machine learning component 602 can utilize in part inference-based schemes to facilitate learning one or more patterns associated with the collective machine learning data, determining one or more rules associated with collective machine learning data, and/or determining one or more relationships associated with the collective machine learning data that influence determinations and inferences by the health assessment component 114, the task risk assessment component 118 and the response component 124. The machine learning component 602 can further employ any suitable machine-learning based techniques, statistical-based techniques and/or probabilistic-based techniques. The machine learning component 602 can additionally or alternatively employ a reduced set of factors (e.g., an optimized set of factors) to facilitate generating the task capabilities models 714 and/or the task risks models 814 discussed below. For example, the machine learning component 602 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the machine learning component 602 can perform a set of machine learning computations associated with collective machine learning data. For example, the machine learning component 602 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. Any rules, patterns, and/or correlations learned by the machine learning component 602 with respect to the collective machine learning data can further be stored in the by the computing system (e.g., in storage 136 and/or memory 152), applied by the machine learning component 602 to define, and/or update/refine the user profile data 138, the task reference data 140, the risk assessment data 142, the response protocol data, and/or employed by the machine learning component 602 to train and/or retrain the task capabilities models 714 and/or the task risks models 814 discussed below.

Figure 7:
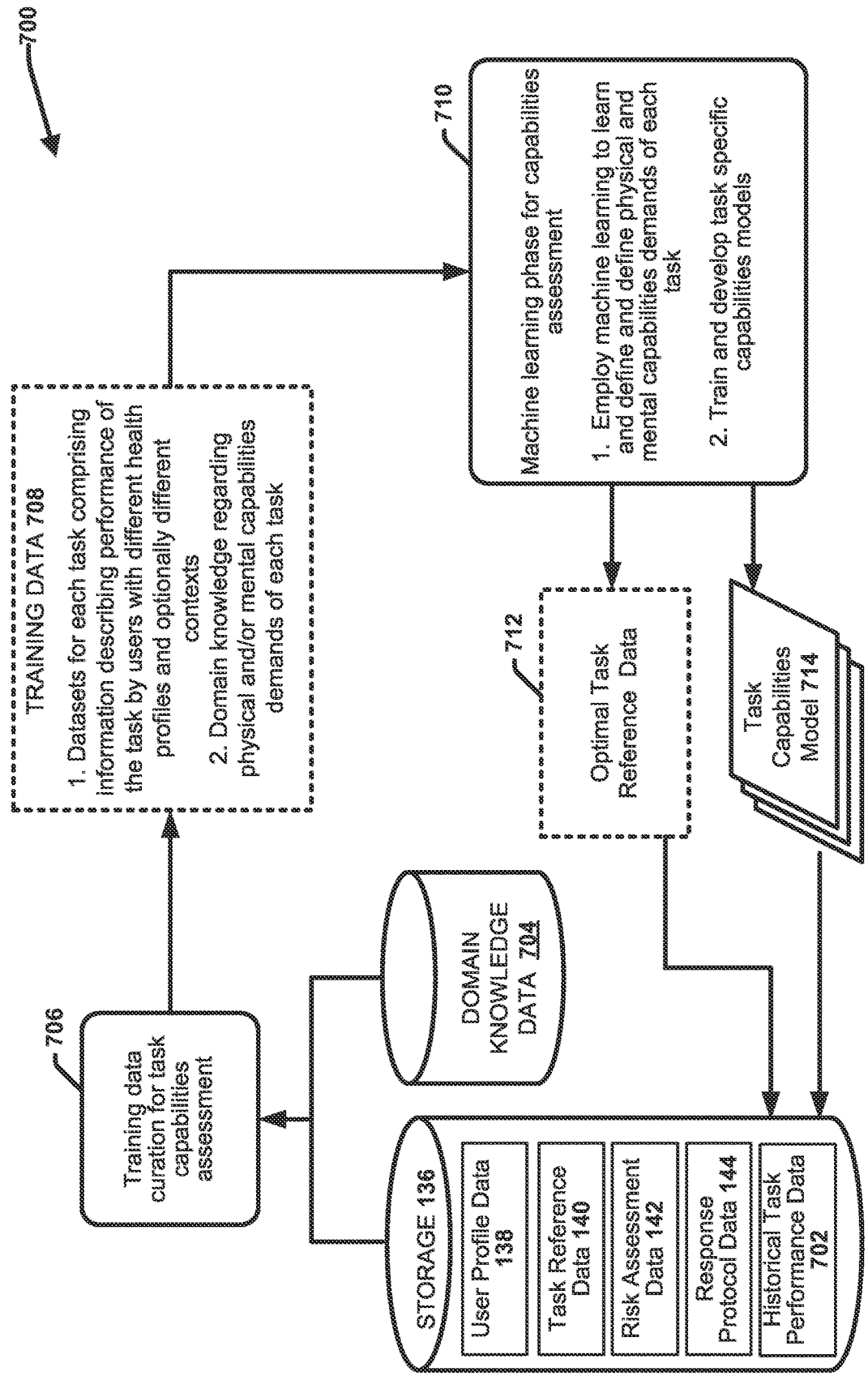
FIG. 7 presents an example machine learning framework that facilitates predicting and minimizing risks associated with performance of physical tasks in accordance with one or more embodiments of the disclosed subject matter.

FIG. 7 presents an example machine learning framework 700 that facilitates predicting and minimizing risks associated with performance of physical tasks in accordance with one or more embodiments of the disclosed subject matter. The machine learning framework 700 provides a high-level framework of one or more machine learning processes that can be performed by the machine learning component 602 to generate optimal task reference data 140 and/or task capabilities models 714 configured to generate information regarding how a user's current physical and/or mental health status lines up with (e.g., deviates from and/or meets) the physical and/or mental health demands of different tasks.

In accordance with framework 600, at 706 the machine learning component 602 can perform training data curation for the capabilities assessment. In some embodiments, this training data curation process can involve parsing through all the data available to the machine learning component 602 to identify and extract information that defines or indicates the physical and/or mental health demands of various physical task and further indicates the optimal, maximum and/or minimum physical and/or mental health capability parameters for each task to be performed safely and/or successfully. As described above, the machine learning component 602 can employ any of the collective machine learning data described above to perform the training data curation 706. In the embodiment shown, the data available to the machine learning component can further include historical task performance data 702 and domain knowledge data 704. The historical task performance data 702 can comprise information describing performance of different tasks by different users with different health profiles and under different contexts. The historical task performance data 702 can include information regarding whether the task was completed and any impacts of the task on the respective users physical and/or mental health. In this regard, the historical task performance data can identify any injuries and/or damage that resulted and information describing the degree of injuries (e.g., a measure of costs attributed to injury and/or damage). The damages and/or injuries can be considered risks. In various embodiments, the historical task performance data 702 can be collected and generated by the computing system 100 based on logged information task risk assessment information gather for respective user over time. With these embodiments, the computing system 100 can determine and receive results information for the respective users regarding whether and to what degree the tasks are completed safely and/or effectively (e.g., to completion), and information regarding any injuries and/or damages incurred (e.g., to the user, other users and/or equipment) attributed to performance of the tasks (as well as costs attributed to the injuries and/or damage). The domain knowledge data 704 can similarly include expert knowledge, scholarly articles and documentation regarding physical and/or mental demands of different tasks, preferred parameters and values, risk associated with the tasks and information regarding how different health profiles (e.g., including known injuries and other comorbidities) influence the risks.

In one or more embodiments, as a result of the training data curation process, the machine learning component 602 can generate training data 708. The training data can include datasets for each task comprising information describing performance of the tasks by users with different health profiles and optionally different contexts (e.g., environmental factors and other contextual factors). The training data 708 can also include domain knowledge regarding physical and mental capabilities demands for each task.

At 710, the machine learning component 602 can perform the machine learning phase of the one or more machine learning processes for the capabilities assessment. In this regard, in some embodiments, at 710, using the training data 708, the machine learning component 602 can employ one or more machine learning processes to learn and define an optimal task reference data 712 for each task as a function of learned correlations, patterns and/or rules between the various health profile parameters and parameter values associated therewith. With these embodiments, the optimal task reference data 712 can be used to define and update the task reference data 140 accordingly.

Additionally, or alternatively, at 710, the machine learning component 602 can train and develop task capabilities models 714 using the training data 708. For example, in some embodiments, the task capabilities models 714 can include separate models tailored to different tasks. The input to each model can include the current health status capabilities parameters for a user, and the output of each model can include information regarding whether and how the user's capabilities satisfy and/or deviate from the preferred physical and/or mental performance capabilities metrics for the task. The task capabilities models once trained can be included with the task reference data 140 and applied by the ability analysis component 120 at runtime to assess the capabilities of a user to perform a task given their current health status data 102. In this regard, the task capabilities models 714 can respectively include or correspond to machine learning models. The task capabilities models 714 can employ various types of ML algorithms, including (but not limited to): deep learning models, neural network models, deep neural network models (DNNs), convolutional neural network models (CNNs), generative adversarial neural network models (GANs), transformers, and the like.

Figure 8:
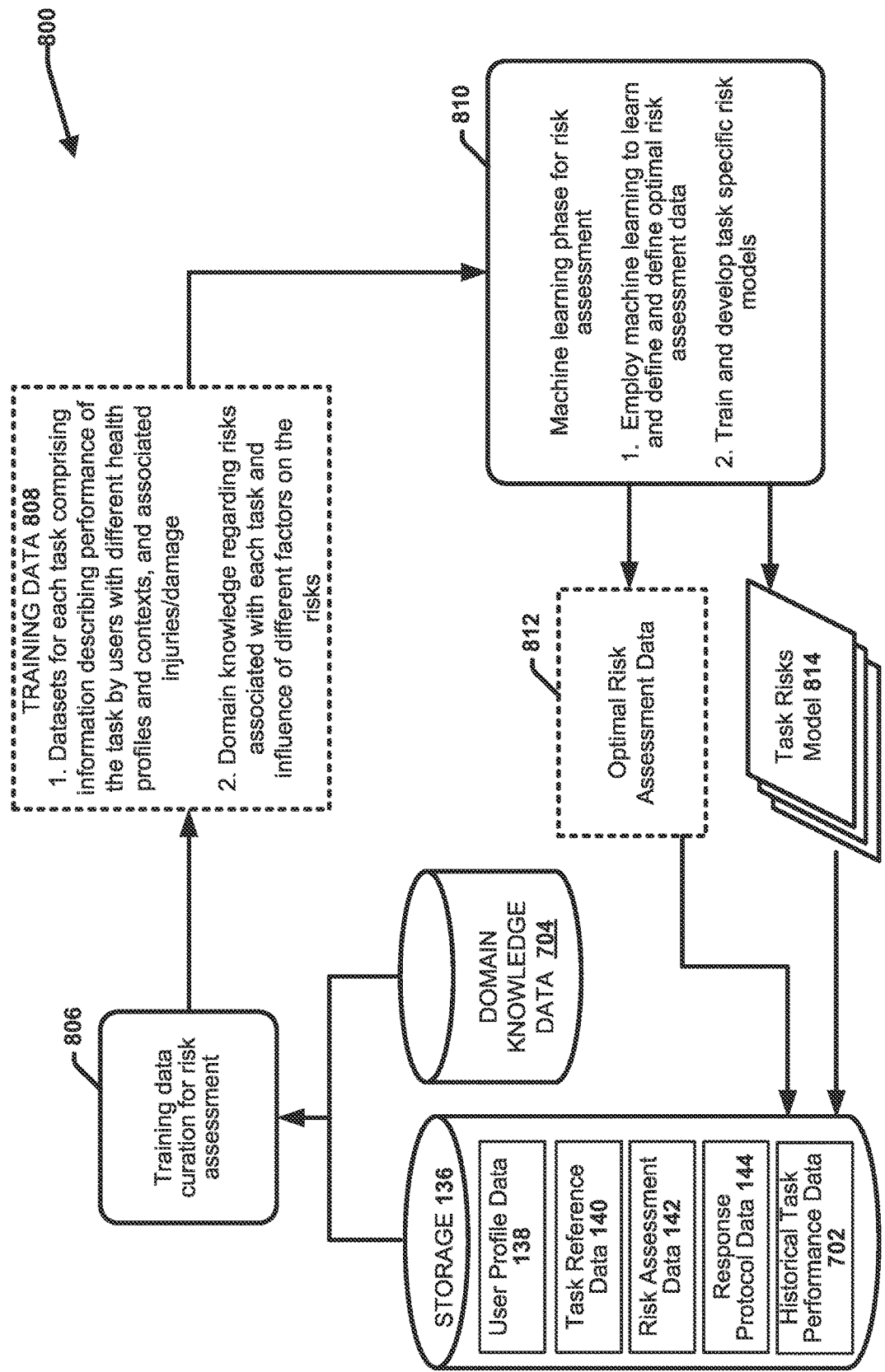
FIG. 8 presents another example machine learning framework that facilitates predicting and minimizing risks associated with performance of physical tasks in accordance with one or more embodiments of the disclosed subject matter.

FIG. 8 presents another example machine learning framework 800 that facilitates predicting and minimizing risks associated with performance of physical tasks in accordance with one or more embodiments of the disclosed subject matter. The machine learning framework 800 provides a high-level framework of one or more machine learning processes that can be performed by the machine learning component 602 to generate optimal risk assessment data 142 and/or task capabilities models 814 configured to generate risk information regarding potential risks associated with different tasks and probabilities of occurrence of the respective risks based on a user's health profile, environment and other contextual factors.

In accordance with framework 700, at 806 the machine learning component 602 can perform training data curation for the risk assessment. In some embodiments, this training data curation process can involve parsing through all the data available to the machine learning component 602 to identify and extract information that defines or indicates any risks associated with performance of different tasks, factors correlated to the risks (e.g., health profile factors, environmental factors and other contextual factors) and the manner in which the respective factors influence the probability of occurrence of the risks. The machine learning component 602 can employ any of the collective machine learning data described above to perform the training data curation at 806, including the historical task performance data 702 and domain knowledge data 704.

In one or more embodiments, as a result of the training data curation process, the machine learning component 602 can generate training data 808. The training data can include datasets for each task comprising information describing performance of the tasks by users with different health profiles and different contexts and associated injuries and/or damages observed. The training data 808 can also include domain knowledge regarding known risks associated each task and the influence of different factors (e.g., health profile factors, contextual factors, etc.) on the probability of occurrence of the risks. In some embodiments injury severity can be accounted for in association with defining separate risks for the same type of injury, wherein the separate risks correspond to different severity levels of the same type of injury (e.g., risk of back injury, risk of minor back injury, risk of moderate back injury, risk of severe back injury).

At 810, the machine learning component 602 can perform the machine learning phase of the one or more machine learning processes for the risk assessment. In this regard, in some embodiments, at 810, using the training data 808, the machine learning component 602 can employ one or more machine learning processes to learn and define optimal risk assessment data 812 for each task as a function of learned correlations, patterns and/or rules between the different risks associated with respective tasks and how various factors influence the probability of occurrence and/or severity of the risks. The machine learning component 602 can also learn how different injuries and/or comorbidities relate to the different risks. With these embodiments, the optimal risk assessment data 812 can be used to define and update the risk assessment data 142 accordingly.

Additionally, or alternatively, at 810, the machine learning component 602 can train and develop task specific risk models 814 using the training data 808. For example, in some embodiments, the task risks models can include separate models tailored to different tasks. The input to each model can include the current health status capabilities parameters for a user and/or the output of the capabilities assessment, which can include information identifying the degree of deviation between the preferred mental and/or physical metrics for a task and the user's corresponding current health status based mental and/or physical metrics. The output of each task risk model 814 can include information identifying all potential risks associated with performance of the task and the risk probabilities. In some embodiments, each task risks model can comprise separate sub-models tailored to different risks (e.g., different injuries, risks to others, risks to equipment, etc.). The task risks models 814 can account for various additional factors aside from the capabilities data, including known injuries and/or other medical conditions of the user (e.g., diseases, mental conditions, etc.) and various environmental factors and other contextual factors. The task risks models once trained can be included with the risk assessment data 142 and applied by the risk analysis component 122 at runtime to assess the risk associated with a user performing a particular task in a particular context and/or environment. In this regard, the task risks models 814 can respectively include or correspond to machine learning models. The task risks models 814 can employ various types of ML algorithms, including (but not limited to): deep learning models, neural network models, deep neural network models (DNNs), convolutional neural network models (CNNs), generative adversarial neural network models (GANs), transformers, and the like.

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 9:
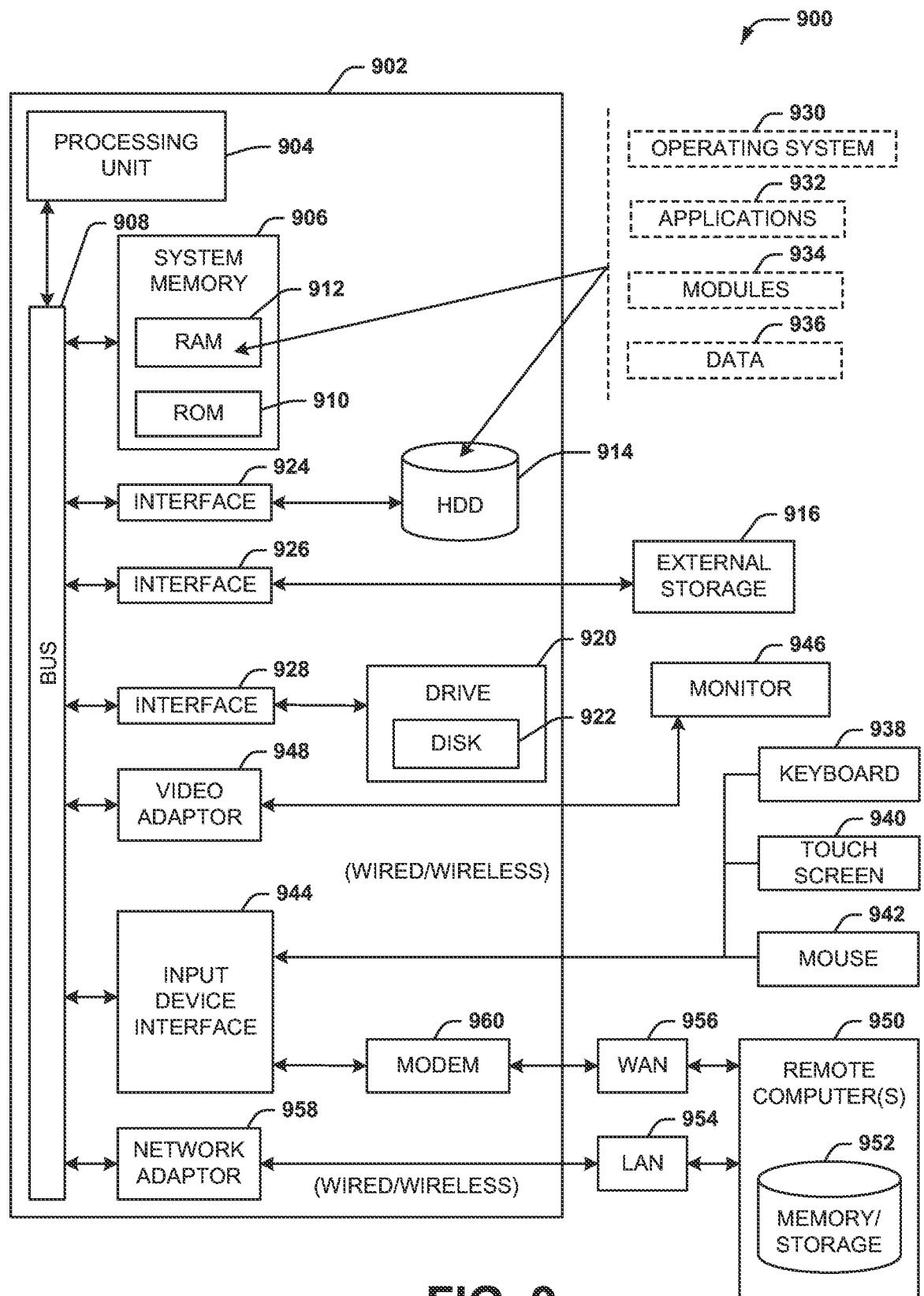
FIG. 9 illustrates a block diagram of an example, non-limiting operating environment in which one or more embodiments described herein can be facilitated.

In order to provide additional context for various embodiments described herein, FIG. 9 and the following discussion are intended to provide a brief, general description of a suitable computing environment 900 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 9, the example environment 900 for implementing various embodiments of the aspects described herein includes a computer 902, the computer 902 including a processing unit 904, a system memory 906 and a system bus 908. The system bus 908 couples system components including, but not limited to, the system memory 906 to the processing unit 904. The processing unit 904 can be any of various commercially available processors. Dual microprocessors and other multi-processor architectures can also be employed as the processing unit 904.

The system bus 908 can be any of several types of bus structure that can further interconnect to a memory bus (with or without a memory controller), a peripheral bus, and a local bus using any of a variety of commercially available bus architectures. The system memory 906 includes ROM 910 and RAM 912. A basic input/output system (BIOS) can be stored in a non-volatile memory such as ROM, erasable programmable read only memory (EPROM), EEPROM, which BIOS contains the basic routines that help to transfer information between elements within the computer 902, such as during startup. The RAM 912 can also include a high-speed RAM such as static RAM for caching data.

The computer 902 further includes an internal hard disk drive (HDD) 914 (e.g., EIDE, SATA), one or more external storage devices 916 (e.g., a magnetic floppy disk drive (FDD) 916, a memory stick or flash drive reader, a memory card reader, etc.) and a drive 920, e.g., such as a solid state drive, an optical disk drive, which can read or write from a disk 922, such as a CD-ROM disc, a DVD, a BD, etc. Alternatively, where a solid state drive is involved, disk 922 would not be included, unless separate. While the internal HDD 914 is illustrated as located within the computer 902, the internal HDD 914 can also be configured for external use in a suitable chassis (not shown). Additionally, while not shown in environment 900, a solid state drive (SSD) could be used in addition to, or in place of, an HDD 914. The HDD 914, external storage device(s) 916 and drive 920 can be connected to the system bus 908 by an HDD interface 924, an external storage interface 926 and a drive interface 928, respectively. The interface 924 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 902, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 912, including an operating system 930, one or more application programs 932, other program modules 934 and program data 936. All or portions of the operating system, applications, modules, and/or data can also be cached in the RAM 912. The systems and methods described herein can be implemented utilizing various commercially available operating systems or combinations of operating systems.

Computer 902 can optionally comprise emulation technologies. For example, a hypervisor (not shown) or other intermediary can emulate a hardware environment for operating system 930, and the emulated hardware can optionally be different from the hardware illustrated in FIG. 9. In such an embodiment, operating system 930 can comprise one virtual machine (VM) of multiple VMs hosted at computer 902. Furthermore, operating system 930 can provide runtime environments, such as the Java runtime environment or the .NET framework, for applications 932. Runtime environments are consistent execution environments that allow applications 932 to run on any operating system that includes the runtime environment. Similarly, operating system 930 can support containers, and applications 932 can be in the form of containers, which are lightweight, standalone, executable packages of software that include, e.g., code, runtime, system tools, system libraries and settings for an application.

Further, computer 902 can be enable with a security module, such as a trusted processing module (TPM). For instance with a TPM, boot components hash next in time boot components, and wait for a match of results to secured values, before loading a next boot component. This process can take place at any layer in the code execution stack of computer 902, e.g., applied at the application execution level or at the operating system (OS) kernel level, thereby enabling security at any level of code execution.

A user can enter commands and information into the computer 902 through one or more wired/wireless input devices, e.g., a keyboard 938, a touch screen 940, and a pointing device, such as a mouse 942. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 904 through an input device interface 944 that can be coupled to the system bus 908, but can be connected by other interfaces, such as a parallel port, an IEEE 1394 serial port, a game port, a USB port, an IR interface, a BLUETOOTH® interface, etc.

A monitor 946 or other type of display device can be also connected to the system bus 908 via an interface, such as a video adapter 948. In addition to the monitor 946, a computer typically includes other peripheral output devices (not shown), such as speakers, printers, etc.

The computer 902 can operate in a networked environment using logical connections via wired and/or wireless communications to one or more remote computers, such as a remote computer(s) 950. The remote computer(s) 950 can be a workstation, a server computer, a router, a personal computer, portable computer, microprocessor-based entertainment appliance, a peer device or other common network node, and typically includes many or all of the elements described relative to the computer 902, although, for purposes of brevity, only a memory/storage device 952 is illustrated. The logical connections depicted include wired/wireless connectivity to a local area network (LAN) 954 and/or larger networks, e.g., a wide area network (WAN) 956. Such LAN and WAN networking environments are commonplace in offices and companies, and facilitate enterprise-wide computer networks, such as intranets, all of which can connect to a global communications network, e.g., the Internet.

When used in a LAN networking environment, the computer 902 can be connected to the local network 954 through a wired and/or wireless communication network interface or adapter 958. The adapter 958 can facilitate wired or wireless communication to the LAN 954, which can also include a wireless access point (AP) disposed thereon for communicating with the adapter 958 in a wireless mode.

When used in a WAN networking environment, the computer 902 can include a modem 960 or can be connected to a communications server on the WAN 956 via other means for establishing communications over the WAN 956, such as by way of the Internet. The modem 960, which can be internal or external and a wired or wireless device, can be connected to the system bus 908 via the input device interface 944. In a networked environment, program modules depicted relative to the computer 902 or portions thereof, can be stored in the remote memory/storage device 952. It will be appreciated that the network connections shown are example and other means of establishing a communications link between the computers can be used.

When used in either a LAN or WAN networking environment, the computer 902 can access cloud storage systems or other network-based storage systems in addition to, or in place of, external storage devices 916 as described above, such as but not limited to a network virtual machine providing one or more aspects of storage or processing of information. Generally, a connection between the computer 902 and a cloud storage system can be established over a LAN 954 or WAN 956 e.g., by the adapter 958 or modem 960, respectively. Upon connecting the computer 902 to an associated cloud storage system, the external storage interface 926 can, with the aid of the adapter 958 and/or modem 960, manage storage provided by the cloud storage system as it would other types of external storage. For instance, the external storage interface 926 can be configured to provide access to cloud storage sources as if those sources were physically connected to the computer 902.

The computer 902 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 10:
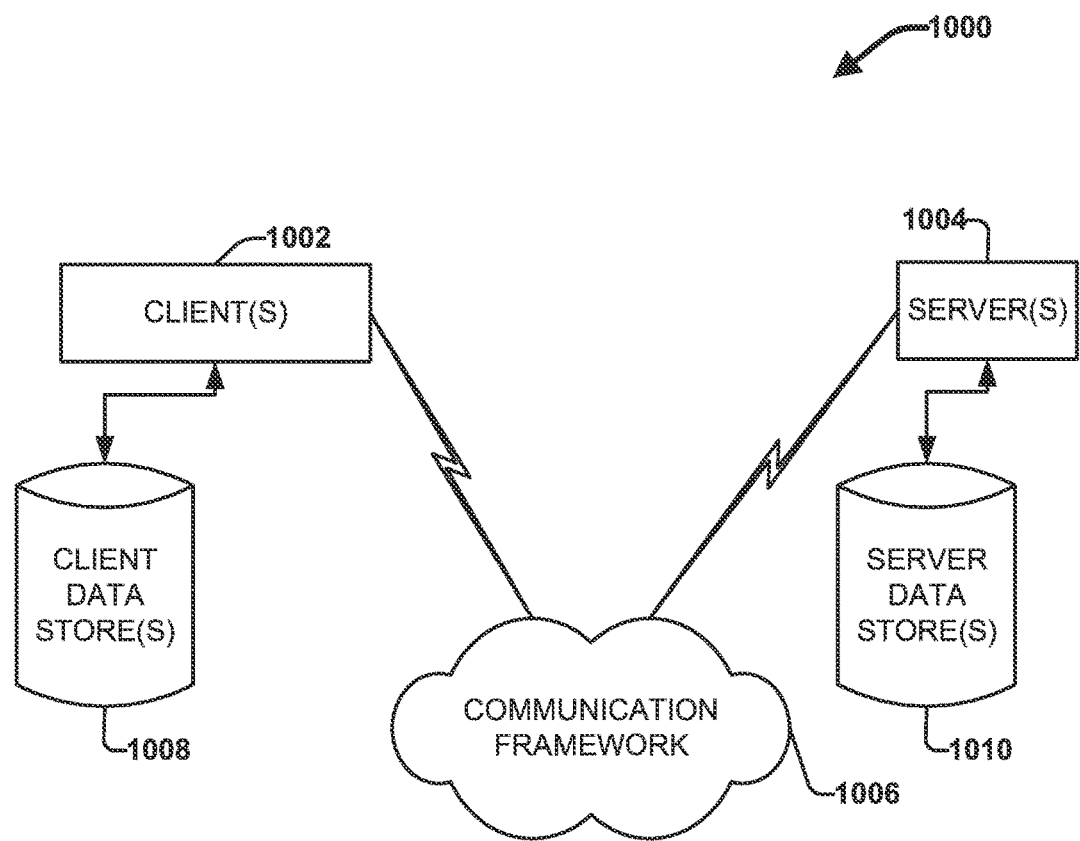
FIG. 10 illustrates a block diagram of another example, non-limiting operating environment in which one or more embodiments described herein can be facilitated.

Referring to FIG. 10, there is illustrated a schematic block diagram of a computing environment 1000 in accordance with this disclosure in which the subject systems (e.g., computing device 101, system 200, computing device 501 and the like), methods and computer readable media can be deployed. The computing environment 1000 includes one or more client(s) 1002 (e.g., laptops, smart phones, PDAs, media players, computers, portable electronic devices, wearable devices, tablets, and the like). The client(s) 1002 can be hardware and/or software (e.g., threads, processes, computing devices). The computing environment 1000 also includes one or more server(s) 1004. The server(s) 1004 can also be hardware or hardware in combination with software (e.g., threads, processes, computing devices). The servers 1004 can house threads to perform transformations by employing aspects of this disclosure, for example. In various embodiments, one or more components, devices, systems, or subsystems of computing device 101, system 200 and computing device 501 can be deployed as hardware and/or software at a client 1002 and/or as hardware and/or software deployed at a server 1004. One possible communication between a client 1002 and a server 1004 can be in the form of a data packet transmitted between two or more computer processes wherein the data packet may include healthcare related data, training data, AI models, input data for the AI models, encrypted output data generated by the AI models, and the like. The data packet can include a metadata, e.g., associated contextual information, for example. The computing environment 1000 includes a communication framework 1006 (e.g., a global communication network such as the Internet, or mobile network(s)) that can be employed to facilitate communications between the client(s) 1002 and the server(s) 1004.

Communications can be facilitated via a wired (including optical fiber) and/or wireless technology. The client(s) 1002 include or are operatively connected to one or more client data store(s) 1008 that can be employed to store information local to the client(s) 1002. Similarly, the server(s) 1004 are operatively include or are operatively connected to one or more server data store(s) 1010 that can be employed to store information local to the servers 1004.

In one embodiment, a client 1002 can transfer an encoded file, in accordance with the disclosed subject matter, to server 1004. Server 1204 can store the file, decode the file, or transmit the file to another client 1002. It is to be appreciated, that a client 1202 can also transfer uncompressed file to a server 1004 can compress the file in accordance with the disclosed subject matter. Likewise, server 1004 can encode video information and transmit the information via communication framework 1006 to one or more clients 1002.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A system, comprising:
  a processor; and
  a memory that stores executable instructions that, when executed by the processor, facilitate performance of operations, comprising:
    obtaining current health status information regarding a current health status of an entity and task information regarding a task to be performed by the entity, wherein the task involves usage of a machine by the entity;
    determining a personalized assessment of an ability of the entity to perform the task based on the current health status information and the task information;
    determining risk information regarding a risk of damage to the machine associated with performance of the task by the entity as a function of the personalized assessment; and
    preventing at least part of the usage of the machine by the entity based on the risk being determined to exceed a defined threshold level of risk.

2. The system of claim 1, wherein determining the personalized assessment is further based on an environment within which the task is to be performed, and wherein determining the risk information is further based on the environment.

3. The system of claim 1, wherein the operations further comprise:
  determining recommendation information regarding whether the entity is to perform the task based on the risk; and
  communicating a recommendation message to a device associated with the entity regarding the recommendation information.

4. The system of claim 3, wherein the operations further comprise:
  tracking entity information, associated with the entity that is received and generated by the system and associating the entity information with health profile information for the entity, the entity information comprising the current health status information, the task information, the risk information and the recommendation information.

5. The system of claim 1, wherein the operations further comprise:
  generating a notification message regarding the risk; and
  communicating the notification message to a device associated with the entity.

6. The system of claim 1, wherein the entity is a first entity, and wherein the operations further comprise:
  generating a notification message regarding the risk; and
  communicating the notification message to a device associated with a second entity other than the first entity.

7. The system of claim 6, wherein the task comprises a group task involved in an activity to be performed by the first entity and the second entity.

8. The system of claim 1, wherein the preventing the at least part of the usage of the machine comprises disabling a functionality of the machine.

9. The system of claim 1, wherein the preventing the at least part of the usage of the machine comprises shutting off a power supply to the machine.

10. The system of claim 1, wherein the operations further comprise:
  determining an action that facilitates reducing the risk based on the current health status information and the task information; and
  communicating recommendation information to a device associated with the entity identifying the action.

11. The system of claim 10, wherein the current health status information relates to at least one of a current mental state or emotional state of the entity, and wherein determining the action comprises determining the action predicted to change the at least one of the current mental state or the emotional state of the entity, respectively, based on a historical action performed by the entity that facilitated the change.

12. A method, comprising:
obtaining, by a system comprising a processor, current health status information representative of a current health status of an entity and task information representative of a task to be performed by the entity, wherein the task involves usage of a machine by the entity;
determining, by the system, a personalized assessment of an ability of the entity to perform the task relative to an environment in which the task is to be performed based on the current health status information and the task information;
determining, by the system, risk information representative of a risk of damage to the machine associated with performance of the task by the entity in the environment as a function of the personalized assessment; and
preventing, by the system, at least part of the usage of the machine by the entity based on the risk determined to exceed a defined threshold level of risk.

13. The method of claim 12, further comprising:
determining, by the system, recommendation information representative of a recommendation of whether the entity is to perform the task based on the risk; and
communicating, by the system to a device associated with the entity, a recommendation message representative of the recommendation.

14. The method of claim 12, wherein the entity is a first entity, and further comprising:
generating, by the system, a notification message comprising a notification of the risk;
communicating, by the system, the notification message to a first device associated with the first entity; and
communicating, by the system, the notification message to a second device associated with a second entity other than the first entity.

15. The method of claim 14, wherein the task comprises a group task involved in an activity to be performed by the first entity and the second entity.

16. The method of claim 12, wherein the preventing the at least part of the usage of the machine comprises sending one or more machine control signals to the machine.

17. The method of claim 12, further comprising:
determining, by the system, an action that facilitates minimizing the risk based on the current health status information and the task information; and
communicating, by the system to a device associated with the entity, recommendation information identifying the action.

18. The method of claim 12, wherein determining the personalized assessment comprises:
predicting an action to be performed by the entity in association with the performance of the task in the environment; and
determining the personalized assessment based on the action.

19. A non-transitory machine-readable medium, comprising executable instructions that, when executed by a processor, facilitate performance of operations, comprising:
obtaining current health status information regarding a current health status of an entity and task information regarding a task to be performed by the entity, wherein the risk involves usage of a machine by the entity;
determining a customized assessment of an ability of the entity to perform the task relative to an environment in which the task is to be performed based on the current health status information and the task information;
determining likelihood information regarding a likelihood of damage to the machine associated with performance of the task by the entity within the environment as a function of the customized assessment; and
preventing at least part of the usage of the machine by the entity based on the likelihood information.

20. The non-transitory machine-readable medium of claim 19, wherein the operations further comprise:
determining recommendation information regarding a recommendation of whether the entity is to perform the task based on the likelihood information; and
communicating a recommendation message to a device associated with the entity in order to notify the entity of the recommendation information.

* * * * *